(12) United States Patent
Wiebensjö et al.

(10) Patent No.: US 10,098,961 B2
(45) Date of Patent: Oct. 16, 2018

(54) HYALURONIC ACID COMPOSITION

(75) Inventors: Åsa Wiebensjö, Uppsala (SE);
Katarina Edsman, Uppsala (SE)

(73) Assignee: Q-MED AB, Uppsala (SE)

( * ) Notice: Subject to any disclaimer, the term of this patent is extended or adjusted under 35 U.S.C. 154(b) by 85 days.

(21) Appl. No.: 13/983,448

(22) PCT Filed: Feb. 3, 2012

(86) PCT No.: PCT/EP2012/051875
§ 371 (c)(1),
(2), (4) Date: Oct. 2, 2013

(87) PCT Pub. No.: WO2012/104419
PCT Pub. Date: Aug. 9, 2012

(65) Prior Publication Data
US 2014/0039061 A1 Feb. 6, 2014

(30) Foreign Application Priority Data
Feb. 3, 2011 (EP) .................................. 11153232

(51) Int. Cl.
| | |
|---|---|
| *A01N 37/18* | (2006.01) |
| *A61K 31/16* | (2006.01) |
| *A61K 47/48* | (2006.01) |
| *A61K 8/42* | (2006.01) |
| *A61K 8/67* | (2006.01) |
| *A61K 8/73* | (2006.01) |
| *A61L 27/20* | (2006.01) |
| *A61L 27/54* | (2006.01) |
| *A61L 31/04* | (2006.01) |
| *A61L 31/16* | (2006.01) |
| *A61Q 7/00* | (2006.01) |
| *A61Q 19/08* | (2006.01) |
| *A61K 8/60* | (2006.01) |
| *A61K 31/167* | (2006.01) |
| *A61K 47/24* | (2006.01) |
| *A61Q 19/00* | (2006.01) |
| *A61K 45/06* | (2006.01) |
| *A61K 31/245* | (2006.01) |
| *A61K 31/375* | (2006.01) |
| *A61K 31/445* | (2006.01) |
| *A61K 31/728* | (2006.01) |
| *A61K 9/00* | (2006.01) |
| *A61K 47/22* | (2006.01) |
| *A61K 47/36* | (2006.01) |

(52) U.S. Cl.
CPC ............ *A61K 47/4823* (2013.01); *A61K 8/42* (2013.01); *A61K 8/602* (2013.01); *A61K 8/676* (2013.01); *A61K 8/735* (2013.01); *A61K 31/167* (2013.01); *A61K 31/245* (2013.01); *A61K 31/375* (2013.01); *A61K 31/445* (2013.01); *A61K 31/728* (2013.01); *A61K 45/06* (2013.01); *A61K 47/24* (2013.01); *A61L 27/20* (2013.01); *A61L 27/54* (2013.01); *A61L 31/042* (2013.01); *A61L 31/16* (2013.01); *A61Q 7/00* (2013.01); *A61Q 19/004* (2013.01); *A61Q 19/007* (2013.01); *A61Q 19/08* (2013.01); *A61K 9/0019* (2013.01); *A61K 47/22* (2013.01); *A61K 47/36* (2013.01); *A61K 2800/91* (2013.01); *A61L 2300/402* (2013.01); *A61L 2400/06* (2013.01); *A61L 2400/16* (2013.01)

(58) Field of Classification Search
None
See application file for complete search history.

(56) References Cited

U.S. PATENT DOCUMENTS

| | | | |
|---|---|---|---|
| 5,087,446 | A | 2/1992 | Suzuki et al. |
| 5,801,192 | A | 9/1998 | Dumas et al. |
| 5,827,937 | A | 10/1998 | Ågerup |
| 2006/0040895 | A1 | 2/2006 | Thacker |
| 2006/0122147 | A1 | 6/2006 | Wohlrab |
| 2009/0017091 | A1 | 1/2009 | Daniloff et al. |
| 2009/0304811 | A1 | 12/2009 | Xia et al. |
| 2010/0028438 | A1 | 2/2010 | Lebreton |
| 2010/0074851 | A1 | 3/2010 | Dubois et al. |
| 2011/0171311 | A1 | 7/2011 | Gousse et al. |

(Continued)

FOREIGN PATENT DOCUMENTS

| | | |
|---|---|---|
| EP | 1 884 231 A1 | 2/2008 |
| EP | 1884231 A1 * | 2/2008 |
| EP | 2033689 A1 | 3/2009 |

(Continued)

OTHER PUBLICATIONS

International Search Report (PCT/ISA/210) dated Mar. 2, 2012, by the European Patent Office as the International Searching Authority for International Application No. PCT/EP2012/051875.

International Preliminary Report on Patentability (PCT/IPEA/409) dated Apr. 11, 2013, by the European Patent Office as the International Searching Authority for International Application No. PCT/EP2012/051875.

E. Abrams et al., "Effect of ascorbic acid on rheumatoid synovial fluid", Ann. Rheum. Dis., 1964, pp. 295-299, vol. 23.

Vivawoman, Sodium Ascorbyl Phosphate: A Stable Vitamin C, pp. 1-13, Nov. 3, 2010.

(Continued)

*Primary Examiner* — Jared D Barsky
(74) *Attorney, Agent, or Firm* — Buchanan Ingersoll & Rooney P.C.

(57) ABSTRACT

An injectable hyaluronic acid composition including a hyaluronic acid; a local anesthetic selected from the group of amide and ester type local anesthetics or a combination thereof; and an ascorbic acid derivative in an amount which prevents or reduces the effect on the viscosity and/or elastic modulus G' of the composition caused by the local anesthetic upon sterilization by heat. Further, the medical and non-medical, such as cosmetic, use of such a composition, and a method of manufacturing such a composition.

6 Claims, 11 Drawing Sheets

(56) References Cited

U.S. PATENT DOCUMENTS

| | | | |
|---|---|---|---|
| 2011/0172180 A1* | 7/2011 | Gousse et al. ............ | 514/54 |
| 2014/0088037 A1 | 3/2014 | Bon Betemps et al. | |

FOREIGN PATENT DOCUMENTS

| | | |
|---|---|---|
| EP | 2 484 387 A1 | 8/2012 |
| JP | 11152204 A | 6/1999 |
| JP | 2013-517263 A | 5/2013 |
| JP | 2014-513988 A | 6/2014 |
| WO | 96/19099 A2 | 6/1996 |
| WO | WO 97/04012 A1 | 2/1997 |
| WO | 98/08550 A1 | 3/1998 |
| WO | 99/49878 A1 | 10/1999 |
| WO | 2005/067994 A1 | 7/2005 |
| WO | WO 2009/005790 A2 | 1/2009 |
| WO | 2010/052430 A2 | 5/2010 |
| WO | 2011/086458 A1 | 7/2011 |
| WO | 2012/097272 A1 | 7/2012 |
| WO | 2013/028904 A2 | 2/2013 |
| WO | 2013/040242 A2 | 3/2013 |
| WO | 2014/032804 A1 | 3/2014 |
| WO | 2007/041627 A1 | 4/2014 |

OTHER PUBLICATIONS

A.I. Segall and M.A. Moyano, "Stability of Vitamin C derivatives in topical formulations containing lipoic acid, vitamin A and E", international Journal Cosmetic Science, vol. 30, pp. 453-458, 2008.

Vivacy Laboratories, Dégradation de la Map au cours de la stérilisation des gels de NaHa + MAP [Degradation of MAP during sterilization of NaHa + MAP gels], not published, tests carried out by Opponent 2, pp. 1-3.

US Pharmacopeia and National Formulary 2010, 2nd Supplement to the USP 33 NF 28, p. R-1107.

* cited by examiner

HYALURONIC ACID COMPOSITION

FIELD OF THE INVENTION

The present invention relates to the field of injectable hyaluronic acid compositions and the use of such compositions in cosmetic and or medical applications.

BACKGROUND

One of the most widely used biocompatible polymers for medical use is hyaluronic acid. It is a naturally occurring polysaccharide belonging to the group of glycosaminoglycans (GAGs). Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Water-absorbing gels, or hydrogels, are widely used in the biomedical field. They are generally prepared by chemical crosslinking of polymers to infinite networks. While native hyaluronic acid and certain crosslinked hyaluronic acid products absorb water until they are completely dissolved, crosslinked hyaluronic acid gels typically absorb a certain amount of water until they are saturated, i.e. they have a finite liquid retention capacity, or swelling degree.

Since hyaluronic acid is present with identical chemical structure except for its molecular mass in most living organisms, it gives a minimum of reactions and allows for advanced medical uses. Crosslinking and/or other modifications of the hyaluronic acid molecule is necessary to improve its duration in vivo. Furthermore, such modifications affect the liquid retention capacity of the hyaluronic acid molecule. As a consequence thereof, hyaluronic acid has been the subject of many modification attempts.

Hyaluronic acid products for injection are often combined with a suitable anaesthetic, e.g. lidocaine, to reduce pain or discomfort experienced by the patient due to the injection procedure.

DESCRIPTION OF THE INVENTION

It is an object of the present invention to provide an improved injectable hyaluronic acid composition for medical and/or non-medical applications.

Hyaluronic acid compositions for use in injection need to be sterilized before use. Sterilization is generally performed by heat treatment, such as autoclaving. The heat treatment generally leads to a reduction of the rigidity or viscosity of the hyaluronic acid composition. As mentioned above, hyaluronic acid products for injection are often combined with a suitable anaesthetic, e.g. lidocaine, to reduce pain or discomfort experienced by the patient due to the injection procedure. It has been observed that the addition of some commonly used anaesthetics, e.g. lidocaine, counteract the effect of the heat treatment on the rheology of a hyaluronic acid composition such that the resulting composition becomes more rigid or viscous than a gel without lidocaine. This change in rheology may be disadvantageous in some applications, for example in applications where shallow injection of the gel is required or desired, and/or where a very fine gauge needle is required or desired. Examples of such applications include skin revitalization and soft tissue augmentation, for example filling of wrinkles or contouring of the face or body, by hyaluronic acid gel injections.

It has now been found that addition of a relatively small amount of an ascorbic acid derivative to a hyaluronic acid composition comprising a local anesthetic selected from the group consisting of amide and ester type local anesthetics may effectively reduce the "viscosity increase" of the hyaluronic acid composition caused by the local anesthetic upon sterilization of the composition by autoclave. Thus, the addition of a relatively small amount of an ascorbic acid derivative to a hyaluronic acid composition comprising a local anesthetic may facilitate the use of finer needles for injection without increasing the force required to expel the composition and without making changes to the hyaluronic acid component. Also, the reduction of the viscosity and/or elastic modulus G' of the solution is advantageous in applications where the composition is injected close to the surface of the skin, for example in skin revitalization or soft tissue augmentation, for example filling of wrinkles or contouring of the face or body, by hyaluronic acid gel injection.

The effect of the ascorbic acid derivative on the viscosity and/or elastic modulus G' on the composition has been shown for both unmodified hyaluronic acids and modified, for example crosslinked, hyaluronic acids, which indicates that it is common to all compositions comprising hyaluronic acid.

Besides the advantageous effect on the viscosity and/or elastic modulus G' on the composition, the addition of an ascorbic acid derivative to the composition may also provide further benefits. Ascorbic acid (also known as vitamin C) and its derivatives can act as reducing agents and scavenge aggressive oxidizing agents and radicals. As ascorbic acid and its derivatives can improve the collagen formation, they may enhance skin morphology. They may also improve epidermal barrier formation, reduce transepidermal water loss, improve wound healing, and thus play an important role in prevention of skin aging and associated dry skin conditions. Ascorbic acid and its derivatives are known for their anti-inflammatory and photoprotective properties as well as their action on the improvement of UV-induced skin damage. It has also been shown that ascorbic acid and its derivatives can clinically improve dermatologic conditions that have inflammation as a component of the disease process, such as psoriasis and asteototic eczema. As ascorbic acid and its derivatives can suppress the formation of melanin, they may also have whitening effect of the skin, and they have been demonstrated to clinically improve melasma and senile freckles. They may also promote hair growth. Ascorbic acid and its derivatives have also been suggested to have anti-cancer properties.

Addition of an ascorbic acid derivative to the hyaluronic acid composition generally has no effect, or little effect, on the stability of the composition. Notably, it has been observed the addition of an ascorbic acid derivative does not increase the stability of the hyaluronic acid composition. Studies by the inventors have shown that the addition of the ascorbic acid derivative may sometimes result in a slight decrease in stability of the hyaluronic acid composition. However, the inventors have found that the advantages associated with adding the ascorbic acid derivative outweigh the slight decrease in stability caused by the addition in some cases. In order to avoid unnecessary decrease in stability of the hyaluronic acid composition the concentration of the ascorbic acid derivative should be kept below the maximum concentrations as set out below.

According to aspects illustrated herein, there is provided an injectable hyaluronic acid composition comprising:
a hyaluronic acid,
a local anesthetic selected from the group consisting of amide and ester type local anesthetics or a combination thereof, and
an ascorbic acid derivative in an amount which prevents or reduces the effect on the viscosity and/or elastic modulus G' of the composition caused by the local anesthetic upon sterilization by heat.

The term "injectable" means that the hyaluronic acid composition is provided in a form which is suitable for parenteral injection, e.g. into soft tissue, such as skin, of a subject or patient. An injectable composition should be sterile and free from components that may cause adverse reactions when introduced into soft tissue, such as the skin, of a subject or patient. This implies that no, or only very mild, immune response occurs in the treated individual. That is, no or only very mild undesirable local or systemic effects occur in the treated individual.

The viscosity and/or elastic modulus G' of the hyaluronic acid composition may be measured according to various methods, well known to the person skilled in the art. Viscosity may for example be measured as the "Zero shear viscosity, $\eta_0$" by rotational viscometry using a Bohlin VOR rheometer (Measuring system C14 or PP 30, Gap 1.00 mm). Other methods of measuring viscosity may also be applicable. The elastic modulus G' may for example be measured using a Bohlin VOR Reometer (Measure system PP 30, Gap 1.00 mm) by performing a strain sweep to find the linear viscoelastic region (LVR) and then measuring the viscoelastic properties within the LVR. Other methods of measuring elastic modulus G' may also be applicable.

The injectable hyaluronic acid composition is preferably aqueous and the hyaluronic acid, the local anesthetic and the ascorbic acid derivative are preferably swelled, dissolved or dispersed in the aqueous phase.

The injectable hyaluronic acid composition comprises a hyaluronic acid. The hyaluronic acid may be a modified, e.g. branched or crosslinked, hyaluronic acid. According to certain embodiments the hyaluronic acid is a crosslinked hyaluronic acid. According to specific embodiments the hyaluronic acid is a hyaluronic acid gel.

Unless otherwise provided, the term "hyaluronic acid" encompasses all variants and combinations of variants of hyaluronic acid, hyaluronate or hyaluronan, of various chain lengths and charge states, as well as with various chemical modifications, including crosslinking. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of —CH$_2$OH groups to —CHO and/or —COOH; periodate oxidation of vicinal hydroxyl groups, optionally followed by reduction, e.g. reduction of —CHO to —CH$_2$OH or coupling with amines to form imines followed by reduction to secondary amines; sulphation; deamidation, optionally followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. Other examples of modifications are isourea, hydrazide, bromocyan, monoepoxide and monosulfone couplings.

The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

In certain embodiments the concentration of said hyaluronic acid is in the range of 1 to 100 mg/ml. In some embodiments the concentration of said hyaluronic acid is in the range of 2 to 50 mg/ml. In specific embodiments the concentration of said hyaluronic acid is in the range of 5 to 30 mg/ml or in the range of 10 to 30 mg/ml. In certain embodiments, the hyaluronic acid is crosslinked. Crosslinked hyaluronic acid comprises crosslinks between the hyaluronic acid chains, which creates a continuous network of hyaluronic acid molecules which is held together by the covalent crosslinks, physical entangling of the hyaluronic acid chains and various interactions, such as electrostatic interactions, hydrogen bonding and van der Waals forces.

Crosslinking of the hyaluronic acid may be achieved by modification with a chemical crosslinking agent. The chemical crosslinking agent may for example selected from the group consisting of divinyl sulfone, multiepoxides and diepoxides. According to embodiments the chemical crosslinking agent is selected from the group consisting of 1,4-butanediol diglycidyl ether (BDDE), 1,2-ethanediol diglycidyl ether (EDDE) and diepoxyoctane. According to a preferred embodiment, the chemical crosslinking agent is 1,4-butanediol diglycidyl ether (BDDE).

The crosslinked hyaluronic acid product is preferably biocompatible. This implies that no, or only very mild, immune response occurs in the treated individual. That is, no or only very mild undesirable local or systemic effects occur in the treated individual.

The crosslinked hyaluronic acid product according to the invention may be a gel, or a hydrogel. That is, it can be regarded as a water-insoluble, but substantially dilute crosslinked system of hyaluronic acid molecules when subjected to a liquid, typically an aqueous liquid.

The gel contains mostly liquid by weight and can e.g. contain 90-99.9% water, but it behaves like a solid due to a three-dimensional crosslinked hyaluronic acid network within the liquid. Due to its significant liquid content, the gel is structurally flexible and similar to natural tissue, which makes it very useful as a scaffold in tissue engineering and for tissue augmentation.

As mentioned, crosslinking of hyaluronic acid to form the crosslinked hyaluronic acid gel may for example be achieved by modification with a chemical crosslinking agent, for example BDDE (1,4-butanediol diglycidylether). The hyaluronic acid concentration and the extent of crosslinking affects the mechanical properties, e.g. the elastic modulus G', and stability properties of the gel. Crosslinked hyaluronic acid gels are often characterized in terms of "degree of modification". The degree of modification of hyaluronic acid gels generally range between 0.1 and 15 mole %. It has been found that the effect of the ascorbic acid derivative on the viscosity and/or elastic modulus G' on the composition in accordance with the present invention is particularly pronounced in crosslinked hyaluronic acid gels with a low degree of modification. The most pronounced effect is obtained in hyaluronic acid gels with a degree of modification of 2 mole % or less, such as 1.5 mole % or less, such as 1.25 mole % or less, for example in the range of 0.1 to 2 mole %, such as in the range of 0.2 to 1.5 mole %, such as in the range of 0.3 to 1.25 mole %, as compared to more crosslinked hyaluronic acid gels. The degree of modification (mole %) describes the amount of crosslinking agent(s) that is bound to HA, i.e. molar amount of bound crosslinking agent(s) relative to the total molar amount of repeating HA disaccharide units. The degree of modification reflects to what degree the HA has been chemically modified by the crosslinking agent. Reaction conditions for crosslinking and suitable analytical techniques for determining the degree of modification are all well known to the person skilled in the art, who easily can adjust these and other relevant factors and thereby provide suitable conditions to obtain a degree of modification in the range of 0.1-2% and verify the resulting product characteristics with respect to the degree of modification. A BDDE (1,4-butanediol diglycidylether) crosslinked hyaluronic acid gel may for example be prepared according to the method described in Examples 1 and 2 of published international patent application WO 9704012.

In a preferred embodiment the hyaluronic acid of the composition is present in the form of a crosslinked hyaluronic acid gel crosslinked by a chemical crosslinking agent, wherein the concentration of said hyaluronic acid is in the range of 10 to 30 mg/ml and the degree of modification with said chemical crosslinking agent is in the range of 0.1 to 2 mole %.

Hyaluronic acid gels may also comprise a portion of hyaluronic acid which is not crosslinked, i.e. not bound to the three-dimensional crosslinked hyaluronic acid network. However, it is preferred that at least 50% by weight, preferably at least 60% by weight, more preferably at least 70% by weight, and most preferably at least 80% by weight, of the hyaluronic acid in a gel composition form part of the crosslinked hyaluronic acid network.

The injectable hyaluronic acid composition further comprises a local anesthetic selected from the group consisting of amide and ester type local anesthetics or a combination thereof. A local anesthetic is a drug that causes reversible local anesthesia and a loss of nociception. When it is used on specific nerve pathways (nerve block), effects such as analgesia (loss of pain sensation) and paralysis (loss of muscle power) can be achieved. The local anesthetic may be added to the hyaluronic acid composition to reduce pain or discomfort experienced by the patient due to the injection procedure. The groups of amide (also commonly referred to as aminoamide) type local anesthetics and ester (also commonly referred to as aminoester) type local anesthetics are well defined and recognized in the art.

Amide and ester type local anesthetic molecules are built on a simple chemical plan, consisting of an aromatic part linked by an amide or ester bond to a basic side-chain. The only exception is benzocaine which has no basic group. All other anesthetics are weak bases, with pKa values mainly in the range 8-9, so that they are mainly but not completely, ionized at physiological pH. As a result of their similarity they may be expected to have similar chemical and physical effects on the hyaluronic acid composition.

According to certain embodiments the local anesthetic is selected from the group consisting of amide and ester type local anesthetics, for example bupivacaine, butanilicaine, carticaine, cinchocaine (dibucaine), clibucaine, ethyl parapiperidinoacetylaminobenzoate, etidocaine, lignocaine (lidocaine), mepivacaine, oxethazaine, prilocalne, ropivacaine, tolycaine, trimecaine, vadocaine, articaine, levobupivacaine, amylocalne, cocaine, propanocaine, clormecaine, cyclomethycaine, proxymetacaine, amethocaine (tetracaine), benzocaine, butacaine, butoxycaine, butyl aminobenzoate, chloroprocaine, dimethocaine (larocaine), oxybuprocaine, piperocaine, parethoxycaine, procaine (novocaine), propoxycaine, tricaine or a combination thereof.

According to certain embodiments the local anesthetic is selected from the group consisting amide type local anesthetics, for example bupivacaine, butanilicaine, carticaine, cinchocaine (dibucaine), clibucaine, ethyl parapiperidinoacetylaminobenzoate, etidocaine, lignocaine (lidocaine), mepivacaine, oxethazaine, prilocalne, ropivacaine, tolycaine, trimecaine, vadocaine, articaine, levobupivacaine or a combination thereof. According to some embodiments the local anesthetic is selected from the group consisting of bupivacaine, lidocaine, and ropivacaine, or a combination thereof. According to specific embodiments the local anesthetic is lidocaine. Lidocaine is a well-known substance, which has been used extensively as a local anesthetic in injectable formulations, such as hyaluronic acid compositions.

The concentration of the amide or ester local anesthetic may be selected by the skilled person within the therapeutically relevant concentration ranges of each specific local anesthetic or a combination thereof.

In certain embodiments the concentration of said local anesthetic is in the range of 0.1 to 30 mg/ml. In some embodiments the concentration of said local anesthetic is in the range of 0.5 to 10 mg/ml.

When lidocaine is used as the local anesthetic, the lidocaine may preferably be present in a concentration in the range of 1 to 5 mg/ml, more preferably in the range of 2 to 4 mg/ml, such as in a concentration of about 3 mg/ml.

The injectable hyaluronic acid composition further comprises an ascorbic acid derivative. The term "ascorbic acid derivative", as used herein, means ascorbic acid or derivatives of ascorbic acid comprising the general chemical structure of ascorbic acid. Thus, the ascorbic acid derivative may be a compound comprising the chemical structure:

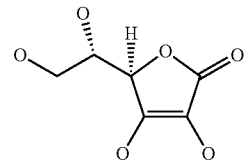

The ascorbic acid derivative of the composition may be ascorbic acid or a compound structurally related to and/or derived from ascorbic acid. Ascorbic acid itself may be useful in some applications, but because of its low stability it may be of limited use in some practical applications.

The ascorbic acid derivative may be water soluble. The solubility of the ascorbic acid derivative in water under atmospheric conditions may preferably be sufficient to allow dissolution of a desired concentration of the ascorbic acid derivative in the composition. The solubility of the water soluble ascorbic acid derivative in water under atmospheric conditions may preferably be sufficient to allow a concentration of 0.001 mg/ml or more, and more preferably 0.01 mg/ml or more, in the hyaluronic acid composition.

The ascorbic acid derivative may be capable of forming ascorbic acid or ascorbate in vivo, for example through enzymatic degradation mediated by phosphatases, glucosidases, etc. Thus, according to an embodiment, the ascorbic acid derivative is capable of forming ascorbic acid or ascorbate when placed in in vivo conditions.

In some embodiments, the ascorbic acid derivative is selected from the group consisting of a phosphate ester of ascorbic acid, a carboxylic acid ester of ascorbic acid, a sulfate of ascorbic acid, a sulfonate ester of ascorbic acid, a carbonate of ascorbic acid and an acetal or ketal substituted ascorbic acid, or a combination thereof.

The ascorbic acid derivative may, for example, be a compound having the general formula:

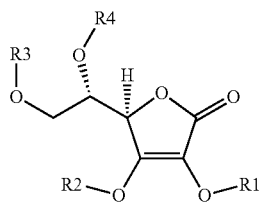
(I)

wherein R1, R2, R3, R4 are, independent of each other, H or an organic substituent. Compound I may for example be a phosphate ester of ascorbic acid, wherein at least one of R1, R2, R3 and R4 is

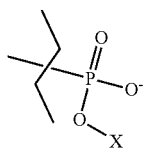

where X is H, alkyl, alkenyl, alkynyl, aryl, an amine, an alcohol, a glycoside, or

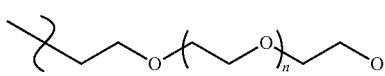

where n can be 0 to 500.

Counter ions can be, but are not limited to, $Na^+$, $K^+$, $Ca^{2+}$, $Al^{3+}$, $Li^+$, $Zn^{2+}$ or $Mg^{2+}$.

Compound I may for example be a carboxylic acid ester of ascorbic acid, wherein at least one of R1, R2, R3 and R4 is

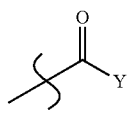

where Y is H, alkyl, alkenyl, alkynyl, aryl, an amine, an alcohol, a glycoside, an amino acid ester or

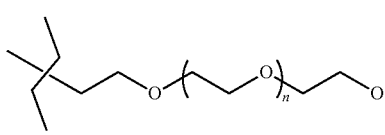

where n can be 0 to 500.

Compound I may for example be a sulfate of ascorbic acid, wherein at least one of R1, R2, R3 and R4 is

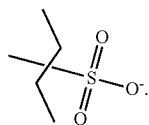

Counter ions can be, but are not limited to, $Na^+$, $K^+$, $Ca^{2+}$, $Al^{3+}$, $Li^+$, $Zn^{2+}$ or $Mg^{2+}$.

Compound I may for example be a sulfonate ester of ascorbic acid, wherein at least one of R1, R2, R3 and R4 is

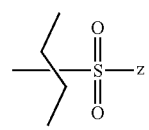

where Z is H, alkyl, alkenyl, alkynyl, aryl, an amine, an alcohol, a glycoside, or

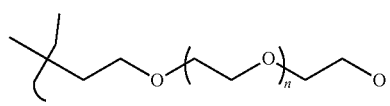

where n can be 0 to 500.

Compound I may for example be a carbonate of ascorbic acid, wherein at least one of R1, R2, R3 and R4 is

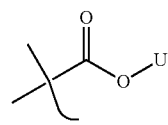

where U is H, alkyl, alkenyl, alkynyl, aryl, an amine, an alcohol, a glycoside, or

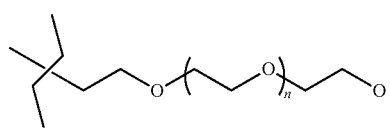

where n can be 0 to 500.

Compound I may for example be an acetal or ketal substituted ascorbic acid, wherein at least one of R1, R2, R3 and R4 is

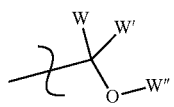

where W, W', and W" are H, alkyl, alkenyl, alkynyl, aryl, an amine, an alcohol, or a carbohydrate residue, for example:

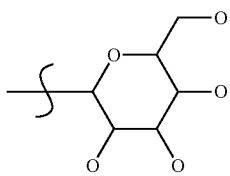

Compound I may for example be an acetal or ketal substituted ascorbic acid having the general formula:

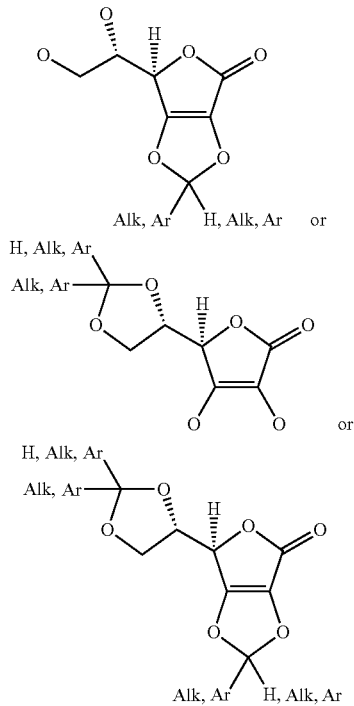

where H is hydrogen, Alk is alkyl and Ar is aryl.

In some embodiments, the ascorbic acid derivative is selected from the group consisting of ascorbyl phosphates, ascorbyl sulfates, and ascorbyl glycosides, or a combination thereof.

In certain embodiments the ascorbic acid derivative is selected from the group consisting of ascorbyl phosphates and ascorbyl glycosides, or a combination thereof.

In some embodiments the ascorbyl phosphate is selected from the group consisting of sodium ascorbyl phosphate (SAP) and magnesium ascorbyl phosphate (MAP), or a combination thereof. Ascorbyl phosphates convert to vitamin C in vivo by enzymatic hydrolysis by phosphatases.

In some embodiments, the ascorbic acid derivative is an aminoalkyl ascorbyl phosphate. In certain embodiments, the ascorbic acid derivative is aminopropyl ascorbyl phosphate.

In some embodiments, the ascorbic acid derivative is ascorbyl glucoside. Ascorbyl glucoside converts to vitamin C in vivo by enzymatic hydrolysis by glucosidases.

In some embodiments, the ascorbic acid derivative is methylsilanol ascorbate.

In some embodiments, the ascorbic acid derivative is L-ascorbic acid acetonide.

The ascorbic acid derivatives described herein may be in unprotonated or fully or partially protonated form, or in the form a pharmaceutically acceptable salt. Specifically, the terms ascorbyl phosphate, ascorbyl sulfate, aminoalkyl ascorbyl phosphate, aminopropyl ascorbyl phosphate, ascorbyl glycoside and ascorbyl glucoside, as used herein, are intended to encompass the compounds in unprotonated or fully or partially protonated form, or in the form a pharmaceutically acceptable salt. Examples of suitable counter ions include, but are not limited to, aluminum, calcium, lithium, magnesium, potassium, sodium, and zinc.

The concentration of the ascorbic acid derivative may be selected by the skilled person depending on the specific ascorbic acid derivative used.

In certain embodiments the concentration of said ascorbic acid derivative is in the range of 0.001 to 15 mg/ml. In certain embodiments the concentration of said ascorbic acid derivative is in the range of 0.001 to 10 mg/ml. In some embodiments the concentration of said ascorbic acid derivative is in the range of 0.01 to 5 mg/ml. A concentration of said ascorbic acid derivative of above 0.01 mg/ml is preferred since it provides a more marked reduction in viscosity and/or elastic modulus G' of the hyaluronic acid composition. A concentration of said ascorbic acid derivative of below 5 mg/ml is preferred since higher concentrations may result in unnecessary decrease of stability of the hyaluronic acid composition without additional benefits.

The required concentration of the ascorbic acid derivative may vary within the above specified ranges depending on the particular ascorbic acid derivative used. As an example, a suitable concentration of sodium ascorbyl phosphate (SAP) or magnesium ascorbyl phosphate (MAP) may be in the range of 0.01 to 1 mg/ml, while a suitable concentration of ascorbyl glucoside may be in the range of 0.1 to 5 mg/ml.

Thus, according to an embodiment, the ascorbic acid derivative is sodium ascorbyl phosphate (SAP) or magnesium ascorbyl phosphate (MAP) in a concentration in the range of 0.01 to 1 mg/ml and preferably in the range of 0.01 to 0.5 mg/ml.

According to another embodiment, the ascorbic acid derivative is ascorbyl glucoside in a concentration in the range of 0.01 to 1 mg/ml, preferably in the range of 0.01 to 0.8 mg/ml, and more preferably in the range of 0.05 to 0.4 mg/ml.

As mentioned, it has been observed the addition of an ascorbic acid derivative does not increase the stability of the hyaluronic acid composition. In other words, the injectable hyaluronic acid composition according to the present invention does not exhibit increased stability compared to the same composition without an ascorbic acid derivative.

The term stability, as used herein, is used to denote the ability of the hyaluronic acid composition to resist degradation during storage and handling prior to use. It is known that the addition of constituents to a hyaluronic acid or hyaluronic acid gel may affect the stability of said hyaluronic acid or hyaluronic acid gel. Stability of hyaluronic acid or hyaluronic acid gel composition can be determined by a range of different methods. Methods for determining stability include, but are not limited to, assessing homogeneity, color, clarity, pH, gel content and rheological properties of the composition. Stability of a hyaluronic acid composition is often determined by observing or measuring one or more of said parameters over time. Stability may for example be determined by measuring the viscosity and/or elastic modulus G' of the hyaluronic acid composition over time. Viscosity may for example be measured as the "Zero shear viscosity, $\eta_0$" by rotational viscometry using a Bohlin VOR rheometer (Measuring system C14 or PP 30, Gap 1.00 mm). Other methods of measuring viscosity may also be applicable. The elastic modulus G' may for example be measured using a Bohlin VOR Reometer (Measure system PP 30, Gap 1.00 mm) by performing a strain sweep to find the linear viscoelastic region (LVR) and then measuring the viscoelastic properties within the LVR. Other methods of measuring elastic modulus G' may also be applicable.

In a more specific embodiment, there is provided an injectable hyaluronic acid composition, comprising: an aqueous hyaluronic acid gel comprising 2 to 50 mg/ml of a hyaluronic acid; 0.5 to 10 mg/ml of lidocaine; and 0.01 to 5 mg/ml of an ascorbic acid derivative selected from the group consisting of ascorbyl phosphates and ascorbyl glycosides, or a combination thereof.

In a more specific embodiment, there is provided an injectable hyaluronic acid composition, comprising: an aqueous hyaluronic acid gel comprising 2 to 50 mg/ml of a hyaluronic acid; 0.5 to 10 mg/ml of lidocaine; and 0.01 to 5 mg/ml of an ascorbyl phosphate, for example sodium or magnesium ascorbyl phosphate.

In another more specific embodiment, there is provided an injectable hyaluronic acid composition, comprising: an aqueous hyaluronic acid gel comprising 2 to 50 mg/ml of a hyaluronic acid; 0.5 to 10 mg/ml of lidocaine; and 0.01 to 5 mg/ml of an ascorbyl glycoside, for example ascorbyl glucoside.

In some embodiments, the composition has been subjected to sterilization. In certain embodiments is the composition sterilized, i.e. the composition has been subjected to heat and/or steam treatment in order to sterilize the composition. In some embodiments the composition has been subjected to sterilization by autoclaving or similar sterilization by heat or steam. Sterilization, e.g. autoclaving, may be performed at a $F_0$-value≥4. The $F_0$ value of a saturated steam sterilisation process is the lethality expressed in terms of the equivalent time in minutes at a temperature of 121° C. delivered by the process to the product in its final container with reference to micro-organisms posessing a Z-value of 10.

When hyaluronic acid compositions are subjected to sterilization by treatment with heat or steam, the viscosity and/or elastic modulus G' are generally reduced. When an amide or ester type local anesthetic is added to the hyaluronic acid composition, this reduction in viscosity and/or elastic modulus G' is decreased, resulting in a firmer or more viscous final product. The addition of the ascorbic acid derivative counteracts this effect of the local anesthetic, thereby producing a final product, having a viscosity and/or elastic modulus G' more closely resembling those of the hyaluronic acid composition without the local anesthetic, without making changes to the hyaluronic acid component.

The crosslinked hyaluronic acid product according to the invention, or an aqueous composition thereof, may be provided in the form of a pre-filled syringe, i.e. a syringe that is pre-filled with a crosslinked hyaluronic acid composition and autoclaved.

The injectable hyaluronic acid compositions described herein may be employed in medical as well as non-medical, e.g. purely cosmetic, procedures by injection of the composition into soft tissues of a patient or subject. The compositions have been found useful in, e.g., soft tissue augmentation, for example filling of wrinkles, by hyaluronic acid gel injection. The compositions have been found especially useful in a cosmetic treatment, referred to herein as skin revitalization, whereby small quantities of the hyaluronic acid composition are injected into the dermis at a number of injection sites distributed over an area of the skin to be treated, resulting in improved skin tone and skin elasticity.

Skin revitalization is a simple procedure and health risks associated with the procedure are very low. According to other aspects illustrated herein, there is provided an injectable hyaluronic acid composition as described above for use as a medicament. The composition is useful, for example in the treatment of various dermatological conditions. Particularly, there is provided an injectable hyaluronic acid composition as described above for use in a dermatological treatment selected from the group consisting of wound healing, treatment of dry skin conditions or sun-damaged skin, treatment of hyper pigmentation disorders, treatment and prevention of hair loss, and treatment of conditions that have inflammation as a component of the disease process, such as psoriasis and asteotic eczema. In other words, there is provided an injectable hyaluronic acid composition as described above for use in the manufacture of a medicament for use in a dermatological treatment selected from the group consisting of wound healing, treatment of dry skin conditions or sun-damaged skin, treatment of hyper pigmentation disorders, treatment and prevention of hair loss, and treatment of conditions that have inflammation as a component of the disease process, such as psoriasis and asteotic eczema.

According to another embodiment there is provided an injectable hyaluronic acid composition as described above for use in the treatment of a joint disorder by intraarticular injection.

According to other aspects illustrated herein, there is provided the use of an injectable hyaluronic acid composition as described above for cosmetic, non-medical, treatment of a subject by injection of the composition into the skin of the subject. A purpose of the cosmetic, non-medical, treatment may be for improving the appearance of the skin, preventing and/or treating hair loss, filling wrinkles or contouring the face or body of a subject. The cosmetic, non-medical, use does not involve treatment of any form of disease or medical condition. Examples of improving the appearance of the skin include, but are not limited to, treatment of sun-damaged or aged skin, skin revitalization, skin whitening and treatment of hyper pigmentation disorders such as senile freckles, melasma and ephelides.

According to certain embodiments, there is provided the use of an injectable hyaluronic acid composition as described above for improving the appearance of skin, preventing and/or treating hair loss, filling wrinkles or contouring the face or body of a subject. The use preferably comprises injecting the composition into the cutis and/or subcutis of a human subject. The use of the injectable hyaluronic acid composition for improving the appearance of skin, preventing and/or treating hair loss, filling wrinkles or contouring the face or body of a subject, may be essentially or totally non-medical, e.g. purely cosmetic.

According to certain embodiments, there is provided the use of an injectable hyaluronic acid composition as described above for improving the appearance of skin. According to a preferred embodiment, there is provided the use of an injectable hyaluronic acid composition as described above for skin revitalization.

According to certain embodiments, there is provided the use of an injectable hyaluronic acid composition as described above for preventing and/or treating hair loss.

According to certain embodiments, there is provided the use of an injectable hyaluronic acid composition as described above for filling wrinkles or contouring the face or body of a subject.

According to other aspects illustrated herein, there is provided a method of improving the appearance of skin, preventing and/or treating hair loss, filling wrinkles or contouring the face or body of a subject, comprising:

a) providing an injectable hyaluronic acid composition as described above, and b) injecting said injectable hyaluronic acid composition into the skin of a subject.

In certain embodiments the injectable hyaluronic acid composition is injected into the cutis and/or subcutis.

According to certain embodiments, the method comprises improving the appearance of skin. According to a preferred embodiment, the method comprises skin revitalization.

According to certain embodiments, the method comprises preventing and/or treating hair loss.

According to certain embodiments, the method comprises filling wrinkles or contouring the face or body of a subject.

According to other aspects illustrated herein, there is provided a method of manufacturing a hyaluronic acid composition comprising:

a) mixing a hyaluronic acid, a local anesthetic selected from the group consisting of amide and ester type local anesthetics or a combination thereof, and an ascorbic acid derivative in an amount which prevents or reduces the effect on the viscosity and/or elastic modulus G' of the composition caused by the local anesthetic upon sterilization by heat, and b) subjecting the mixture to sterilization by heat.

In the method of manufacturing the composition, said ascorbic acid derivative is operative for preventing or reducing the effect of the local anesthetic on the viscosity and/or elastic modulus G' of the composition due to the sterilization by heat.

The components of the composition, i.e. hyaluronic acid, local anesthetic and ascorbic acid derivative, may be further defined as described above for the injectable hyaluronic acid composition.

The manufactured hyaluronic acid composition does not exhibit increased stability compared to the same composition without an ascorbic acid derivative.

In some embodiments, the sterilization of step b) comprises subjecting the mixture to a heat treatment. In certain embodiments, the sterilization of step b) comprises autoclaving the mixture at a $F_0$-value≥4. The sterilization may be further characterized as described above for the composition.

According to other aspects illustrated herein, there is provided the use of an ascorbic acid derivative in an injectable hyaluronic acid composition, further comprising a hyaluronic acid and a local anesthetic selected from the group consisting of amide and ester type local anesthetics or a combination thereof, for preventing or reducing the effect of the local anesthetic on the viscosity and/or elastic modulus G' of the composition due to the sterilization by heat.

The components of the composition may be further defined as described above for the injectable hyaluronic acid composition. The sterilization may be further characterized as described above.

The injectable hyaluronic acid composition formed by use of an ascorbic acid derivative does not exhibit increased stability compared to the same composition without an ascorbic acid derivative.

ITEMIZED LISTING OF EMBODIMENTS

Figure 1:
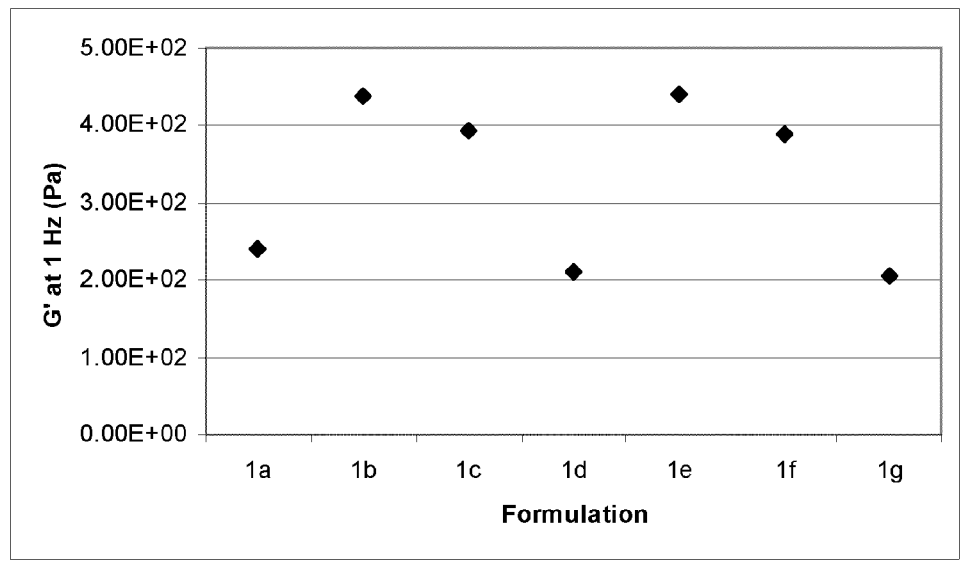
FIG. 1 is a graph showing the effect of MAP (Magnesium Ascorbyl Phosphate) on a hyaluronic acid gel with lidocaine.

1. An injectable hyaluronic acid composition comprising a hyaluronic acid,
   a local anesthetic selected from the group consisting of amide and ester type local anesthetics or a combination thereof, and
   an ascorbic acid derivative in an amount which prevents or reduces the effect on the viscosity and/or elastic modulus G' of the composition caused by the local anesthetic upon sterilization by heat.

2. An injectable hyaluronic acid composition according to item 1, wherein said composition does not exhibit increased stability compared to the same composition without an ascorbic acid derivative.

3. An injectable hyaluronic acid composition according to any one of the preceding items, wherein said hyaluronic acid is a modified hyaluronic acid.

4. An injectable hyaluronic acid composition according to item 3, wherein said hyaluronic acid is a hyaluronic acid gel.

5. An injectable hyaluronic acid composition according to item 4, wherein the hyaluronic acid gel is crosslinked by modification with a chemical crosslinking agent.

6. An injectable hyaluronic acid composition according to item 5, wherein the chemical crosslinking agent is selected from the group consisting of divinyl sulfone, multiepoxides and diepoxides.

7. An injectable hyaluronic acid composition according to item 6, wherein the chemical crosslinking agent is selected from the group consisting of 1,4-butanediol diglycidyl ether (BDDE), 1,2-ethanediol diglycidyl ether (EDDE) and diepoxyoctane.

8. An injectable hyaluronic acid composition according to item 7, wherein the chemical crosslinking agent is 1,4-butanediol diglycidyl ether (BDDE).

9. An injectable hyaluronic acid composition according to any one of items 5-8, wherein the hyaluronic acid gel has a degree of modification of 2 mole % or less, such as 1.5 mole % or less, such as 1.25 mole % or less.

10. An injectable hyaluronic acid composition according to any one of items 5-8, wherein the hyaluronic acid gel has a degree of modification in the range of 0.1 to 2 mole %, such as in the range of 0.2 to 1.5 mole %, such as in the range of 0.3 to 1.25 mole %.

11. An injectable hyaluronic acid composition according to any one of the preceding items, wherein the concentration of said hyaluronic acid is in the range of 1 to 100 mg/ml.

12. An injectable hyaluronic acid composition according to item 11, wherein the concentration of said hyaluronic acid is in the range of 2 to 50 mg/ml.

13. An injectable hyaluronic acid composition according to item 12, wherein the concentration of said hyaluronic acid is in the range of 10 to 30 mg/ml.

14. An injectable hyaluronic acid composition according to any one of the preceding items, wherein said local anesthetic is selected from the group consisting of lignocaine (lidocaine), bupivacaine, butanilicaine, carticaine, cinchocaine (dibucaine), clibucaine, ethylparapiperidinoacetylaminobenzoate, etidocaine, mepivacaine, oxethazaine, prilocalne, ropivacaine, tolycaine, trimecaine, vadocaine, articaine, levobupivacaine, amylocalne, cocaine, propanocaine, clormecaine, cyclomethycaine, proxymetacaine, amethocaine (tetracaine), benzocaine, butacaine, butoxycaine, butyl aminobenzoate, chloroprocaine, dimethocaine (larocaine), oxybuprocaine, piperocaine, parethoxycaine, procaine (novocaine), propoxycaine, tricaine, or a combination thereof.

15. An injectable hyaluronic acid composition according to any one of the preceding items, wherein said local anesthetic is selected from the group consisting of amide type local anesthetics, or a combination thereof.

16. An injectable hyaluronic acid composition according to item 15, wherein said local anesthetic is selected from the group consisting of lignocaine (lidocaine), bupivacaine, butanilicaine, carticaine, cinchocaine (dibucaine), clibucaine, ethyl parapiperidinoacetylaminobenzoate, etidocaine, mepivacaine, oxethazaine, prilocalne, ropivacaine, tolycaine, trimecaine, vadocaine, articaine, levobupivacaine or a combination thereof.

17. An injectable hyaluronic acid composition according to item 16, wherein said local anesthetic is selected from the group consisting of lidocaine, bupivacaine, and ropivacaine, or a combination thereof.

18. An injectable hyaluronic acid composition according to item 17, wherein said local anesthetic is lidocaine.

19. An injectable hyaluronic acid composition according to any one of the preceding items, wherein the concentration of said local anesthetic is in the range of 0.1 to 30 mg/ml.

20. An injectable hyaluronic acid composition according to item 19, wherein the concentration of said local anesthetic is in the range of 0.5 to 10 mg/ml.

21. An injectable hyaluronic acid composition according to item 20, wherein the concentration of said lidocaine is in the range of 1 to 5 mg/ml.

22. An injectable hyaluronic acid composition according to item 21, wherein the concentration of said lidocaine is in the range of 2 to 4 mg/ml.

23. An injectable hyaluronic acid composition according to item 22, wherein the concentration of said lidocaine is about 3 mg/ml.

24. An injectable hyaluronic acid composition according to any one of the preceding items, wherein said ascorbic acid derivative is a compound comprising the chemical structure:

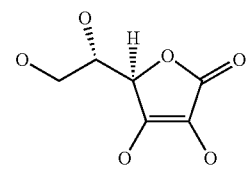

25. An injectable hyaluronic acid composition according to any one of the preceding items, wherein said ascorbic acid derivative is water soluble under atmospheric conditions.

26. An injectable hyaluronic acid composition according to any one of the preceding items, wherein said ascorbic acid derivative is capable of forming ascorbic acid or ascorbate when placed in in vivo conditions.

27. An injectable hyaluronic acid composition according to any one of the preceding items, wherein said ascorbic acid derivative is selected from the group consisting of ascorbyl phosphates, ascorbyl sulfates, and ascorbyl glycosides, or a combination thereof.

28. An injectable hyaluronic acid composition according to any one of the preceding items, wherein said ascorbic acid derivative is selected from the group consisting of ascorbyl phosphates and ascorbyl glycosides, or a combination thereof.

29. An injectable hyaluronic acid composition according to any one of the preceding items, wherein said ascorbic acid derivative is an ascorbyl phosphate.

30. An injectable hyaluronic acid composition according to item 29, wherein said ascorbyl phosphate is selected from the group consisting of sodium ascorbyl phosphate (SAP) and magnesium ascorbyl phosphate (MAP).

31. An injectable hyaluronic acid composition according to any one of items 1-28, wherein said ascorbic acid derivative is an ascorbyl glycoside.

32. An injectable hyaluronic acid composition according to item 31, wherein said ascorbic acid derivative is ascorbyl glucoside.

33. An injectable hyaluronic acid composition according to any one of the preceding items, wherein the concentration of said ascorbic acid derivative is in the range of 0.001 to 15 mg/ml.

34. An injectable hyaluronic acid composition according to item 33, wherein the concentration of said ascorbic acid derivative is in the range of 0.001 to 10 mg/ml.

35. An injectable hyaluronic acid composition according to item 34, wherein the concentration of said ascorbic acid derivative is in the range of 0.01 to 5 mg/ml.

36. An injectable hyaluronic acid composition according to item 35, wherein the concentration of said ascorbic acid derivative is in the range of 0.01 to 0.5 mg/ml.

37. An injectable hyaluronic acid composition according to item 30, wherein the concentration of said sodium ascorbyl phosphate (SAP) or magnesium ascorbyl phosphate (MAP) is in the range of 0.01 to 1 mg/ml.

38. An injectable hyaluronic acid composition according to item 37, wherein the concentration of said sodium ascorbyl phosphate (SAP) or magnesium ascorbyl phosphate (MAP) is in the range of 0.01 to 0.5 mg/ml.

39. An injectable hyaluronic acid composition according to item 31, wherein the concentration of said ascorbyl glucoside is in the range of 0.01 to 0.8 mg/ml.

40. An injectable hyaluronic acid composition according to item 39, wherein the concentration of said ascorbyl glucoside is in the range of 0.05 to 0.4 mg/ml.

41. An injectable hyaluronic acid composition according to item 1, comprising
    an aqueous hyaluronic acid gel comprising 2 to 50 mg/ml of a hyaluronic acid,
    0.5 to 10 mg/ml of lidocaine, and
    0.01 to 5 mg/ml of an ascorbic acid derivative selected from the group consisting of ascorbyl phosphates and ascorbyl glycosides, or a combination thereof.

42. A sterilized injectable hyaluronic acid composition according to any one of the preceding items.

43. A sterilized hyaluronic acid composition according to item 42, wherein the composition has been subjected to sterilization by autoclaving or similar sterilization by heat.

44. An injectable hyaluronic acid composition as defined in any one of items 1-43 for use as a medicament.

45. An injectable hyaluronic acid composition as defined in any one of items 1-43 for use in a dermatological treatment selected from the group consisting of wound healing, treatment of dry skin conditions and sun-damaged skin, treatment of hyper pigmentation disorders, treatment and prevention of hair loss, and treatment of conditions that have inflammation as a component of the disease process, such as psoriasis and asteotoic eczema.

46. An injectable hyaluronic acid composition as defined in any one of items 1-43 for use in the treatment of a joint disorder by intraarticular injection.

47. Cosmetic, non-medical use of an injectable acid composition as defined in any one of items 1-43 for improving the appearance of skin, preventing and/or treating hair loss, filling wrinkles or contouring the face or body of a subject.

48. Cosmetic, non-medical use according to item 47, for improving the appearance of the skin of a subject.

49. Cosmetic, non-medical use according to item 47, for filling wrinkles of a subject.

50. Cosmetic, non-medical method of improving the appearance of skin, preventing and/or treating hair loss, filling wrinkles or contouring the face or body of a subject, comprising
a) providing an injectable hyaluronic acid composition as defined in any one of items 1-43, and
b) injecting said injectable hyaluronic acid composition into the skin of a subject.

51. A method according to item 50, wherein said injectable hyaluronic acid composition is injected into the cutis and/or subcutis.

52. A method of manufacturing a hyaluronic acid composition comprising:
a) mixing a hyaluronic acid, a local anesthetic selected from the group consisting of amide and ester type local anesthetics or a combination thereof, and an ascorbic acid derivative in an amount which prevents or reduces the effect on the viscosity and/or elastic modulus G' of the composition caused by the local anesthetic upon sterilization by heat, and
b) subjecting the mixture to sterilization by heat.

53. A method according to item 52, wherein the formed hyaluronic acid composition does not exhibit increased stability compared to the same composition without an ascorbic acid derivative.

54. A method according any one of items 52 and 53, wherein step b) comprises subjecting the mixture to a $F_0$-value≥4.

55. Use of an ascorbic acid derivative in an injectable hyaluronic acid composition further comprising
    a hyaluronic acid and
    a local anesthetic selected from the group consisting of amide and ester type local anesthetics or a combination thereof, for preventing or reducing the effect of the local anesthetic on the viscosity and/or elastic modulus G' of the composition due to sterilization by heat.

56. Use according to item 55, wherein the hyaluronic acid composition does not exhibit increased stability compared to the same composition without an ascorbic acid derivative.

EXAMPLES

Without desiring to be limited thereto, the present invention will in the following be illustrated by way of examples. Since hyaluronic acid polymer and hyaluronic acid gel may always be subject to some batch to batch variations, each example has been performed with a single batch of hyaluronic acid polymer or hyaluronic acid gel in order to obtain comparable results. Slight variations in, e.g., rheological properties or viscosity between similar compositions in different examples may be due to such batch to batch variations.

Example 1. Hyaluronic Acid Gel with Lidocaine and MAP

In this experiment, the rheological properties after autoclaving of hyaluronic acid gels without additives were compared to hyaluronic acid gels with added lidocaine and hyaluronic acid gels with added lidocaine and MAP respectively.

Formulations having various concentrations lidocaine and MAP as outlined in Table 1 were prepared as described below.

TABLE 1

| Formulation # | HA Gel [mg/ml] | Lidocaine [mg/ml] | MAP [mg/ml] | G' at 1.0 Hz [Pa] |
|---|---|---|---|---|
| 1a | 20 | 0 | 0 | 239 |
| 1b | 20 | 3 | 0 | 437 |
| 1c | 20 | 3 | 0.07 | 394 |
| 1d | 20 | 3 | 0.7 | 211 |
| 1e | 20 | 1 | 0 | 440 |
| 1f | 20 | 1 | 0.07 | 388 |
| 1g | 20 | 1 | 0.7 | 206 |

In all formulations a BDDE (1,4-butandiol diglycidylether) crosslinked hyaluronic acid gel with a degree of modification of 1 mole % and a hyaluronic acid content of 20 mg/ml was used. The degree of modification (mole %) describes the amount of crosslinking agent(s) that is bound to HA, i.e. molar amount of bound crosslinking agent(s) relative to the total molar amount of repeating HA disaccharide units. The degree of modification reflects to what degree the HA has been chemically modified by the crosslinking agent.

The BDDE (1,4-butandiol diglycidylether) crosslinked hyaluronic acid gel may for example be prepared according to the method described in Examples 1 and 2 of published international patent application WO 9704012.

A stock-solution of lidocaine hydrochloride monohydrate (CAS number 6108-05-0, Sigma Aldrich, St. Louis, USA) was prepared by dissolving lidocaine hydrochloride monohydrate in WFI (water for injection) and a stock-solution of Magnesium Ascorbyl Phosphate (MAP, CAS number 114040-31-2, Nikko Chemicals co, Japan), was prepared by dissolving MAP in phosphate buffered saline (8 mM, 0.9% NaCl).

Formulation 1a:

The hyaluronic acid gel was diluted to the same degree as 1b-1g by adding phosphate buffered saline (8 mM, 0.9% NaCl).

Formulation 1b:

Stock-solution of lidocaine was added to the hyaluronic acid gel to a final concentration of 3 mg/ml gel.

Formulation 1c:

Stock-solution of lidocaine and stock-solution of MAP were added to the hyaluronic acid gel to the final concentrations of 3 mg lidocaine/ml and 0.07 mg MAP/ml gel.

Formulations 1d-1g were prepared in the same manner by varying the amounts of lidocaine stock-solution and MAP stock-solution. To all formulations phosphate buffered saline (8 mM, 0.9% NaCl) was added to adjust the dilution to the same degree.

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~30).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

The results are presented in FIG. 1. MAP counteracts the effect on the elastic modulus G' of the composition caused by the local anesthetic upon sterilization by heat. The higher the concentration of MAP the larger is the decrease on the elastic G' modulus. A higher concentration of lidocaine does not affect the increase on the elastic modulus G'.

Example 2. Hyaluronic Acid Gel with a Higher Degree of Modification with Lidocaine and MAP Formulations as outlined in Table 2 were prepared essentially according to the method described in Example 1, with the exception that a hyaluronic acid gel with a higher degree of modification (approximately 7%) was used. The hyaluronic acid gel may for example be prepared according to the method described in the examples of U.S. Pat. No. 6,921,819 B2.

TABLE 2

| Formulation # | HA Gel [mg/ml] | Lidocaine [mg/ml] | MAP [mg/ml] | G' at 1.0 Hz [Pa] |
|---|---|---|---|---|
| 2a | 20 | 0 | 0 | 393 |
| 2b | 20 | 3 | 0 | 417 |
| 2c | 20 | 3 | 0.3 | 388 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~29).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 2:
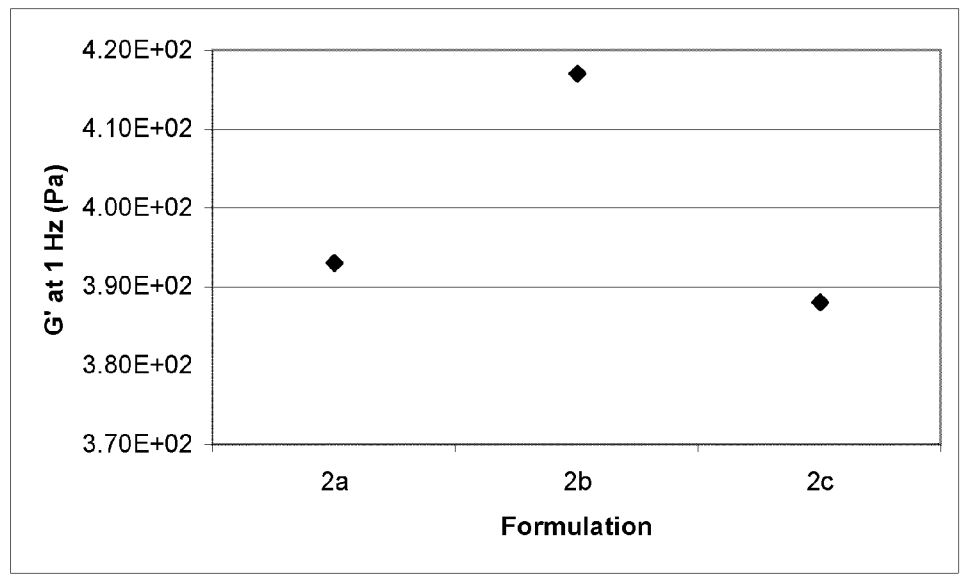
FIG. 2 is a graph showing the effect of MAP on a hyaluronic acid gel with lidocaine.

The results are presented in FIG. 2. MAP counteracts the effect on the elastic modulus G' of the composition caused by the local anesthetic upon sterilization by heat.

Example 3. Non-Crosslinked Hyaluronic Acid with Lidocaine and MAP

Formulations as outlined in Table 3 were prepared essentially according to the method described in Example 1, with the exception that a non-crosslinked hyaluronic acid with an average molecular weight of $1 \times 10^6$ Da was used.

TABLE 3

| Formulation # | HA [mg/ml] | Lidocaine [mg/ml] | MAP [mg/ml] | Zero shear viscosity $\eta_0$ [Pas] |
|---|---|---|---|---|
| 3a | 20 | 0 | 0 | 3.83 |
| 3b | 20 | 3 | 0 | 4.26 |
| 3c | 20 | 3 | 0.07 | 2.45 |
| 3d | 20 | 3 | 0.3 | 1.98 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22).

Figure 3:
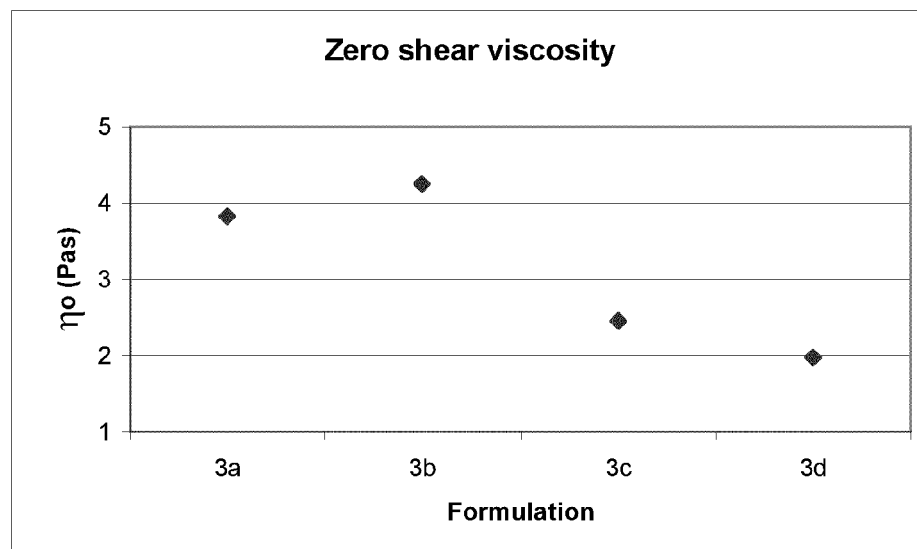
FIG. 3 is a graph showing the effect of MAP on a non-crosslinked hyaluronic acid with lidocaine.

The viscosity of the formulations was studied using rotational viscometry using a Bohlin VOR rheometer (Measure system PP 30, Gap 1.00 mm). The results are presented in FIG. 3. MAP counteracts the effect on the viscosity of the composition caused by the local anesthetic upon sterilization by heat.

Example 4. Non-Crosslinked Hyaluronic Acid with Lidocaine and MAP at Lower Concentrations Formulations as outlined in Table 4 were prepared essentially according to the method described in Example 3, with the exception that lower concentrations of MAP were used.

TABLE 4

| Formulation # | HA [mg/ml] | Lidocaine [mg/ml] | MAP [mg/ml] | Zero shear viscosity $\eta_0$ [Pas] |
|---|---|---|---|---|
| 4a | 20 | 0 | 0 | 5.13 |
| 4b | 20 | 3 | 0 | 6.16 |

TABLE 4-continued

| Formulation # | HA [mg/ml] | Lidocaine [mg/ml] | MAP [mg/ml] | Zero shear viscosity $\eta_0$ [Pas] |
|---|---|---|---|---|
| 4c | 20 | 3 | 0.03 | 5.27 |
| 4d | 20 | 3 | 0.01 | 5.87 |
| 4e | 20 | 3 | 0.005 | 5.91 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22). The viscosity of the formulations was studied using rotational viscometry using a Bohling VOR rheometer (Measure system PP 30, Gap 1.00 mm).

Figure 4:
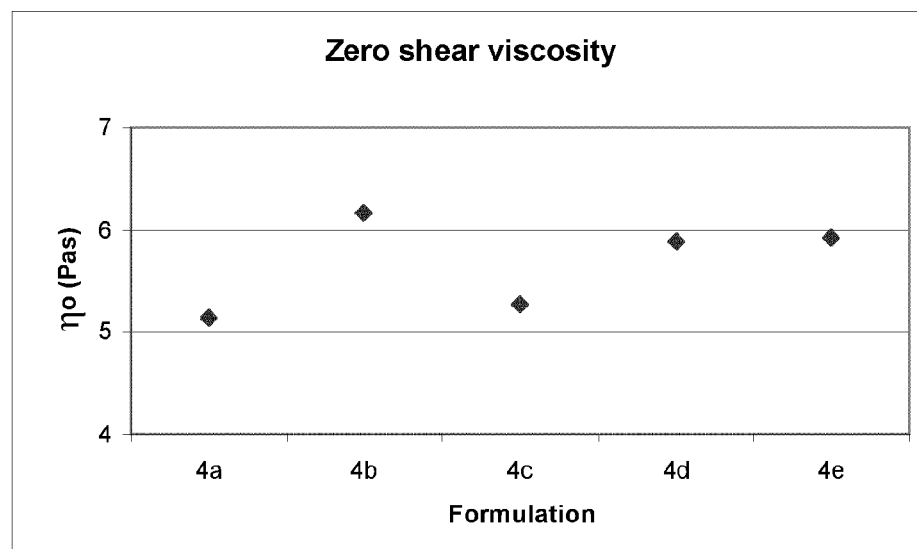
FIG. 4 is a graph showing the effect of MAP on a non-crosslinked hyaluronic acid with lidocaine.

The results are presented in FIG. 4. MAP counteracts the effect on the viscosity of the composition caused by the local anesthetic upon sterilization by heat.

Example 5. Hyaluronic Acid Gel with Lidocaine and MAP Autoclaved at Different $F_0$-Values Formulations as outlined in Table 5 were prepared essentially according to the method described in Example 1, with the exception that a different concentration of MAP was used.

TABLE 5

| Formulation # | HA [mg/ml] | Lidocaine [mg/ml] | MAP [mg/ml] | Average $F_0$ | G' at 1.0 Hz [Pa] |
|---|---|---|---|---|---|
| 5a | 20 | 0 | 0 | 22 | 194 |
| 5b | 20 | 3 | 0 | 22 | 269 |
| 5c | 20 | 3 | 0.3 | 22 | 220 |
| 5d | 20 | 0 | 0 | 6 | 317 |
| 5e | 20 | 3 | 0 | 6 | 363 |
| 5f | 20 | 3 | 0.3 | 6 | 332 |

The pH values of the formulations were adjusted to 7.5±0.2 and the formulations were filled in 1 ml glass syringes (BD Hypak SCF) and autoclaved in a Getinge GEV 6610 ERC-1 autoclave at the different $F_0$-values described in Table 5.

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 5:
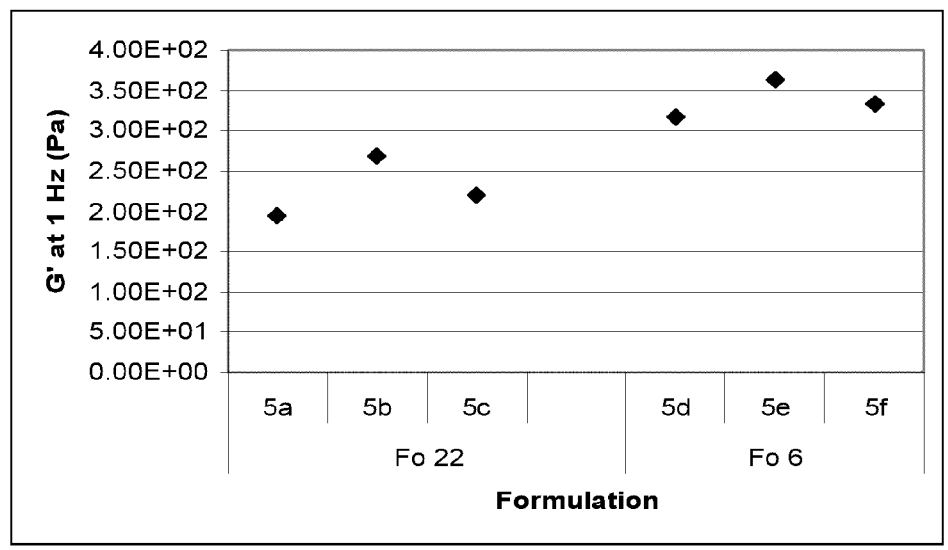
FIG. 5 is a graph showing the effect of MAP on a hyaluronic acid gel with lidocaine autoclaved at various $F_0$ values.

The results are presented in FIG. 5. The effect on the elastic modulus G' of the composition caused by the local anesthetic upon sterilization by heat is slightly larger for the higher $F_0$-value. MAP counteracts the effect on the elastic modulus G' of the composition caused by the local anesthetic upon sterilization by heat.

Example 6. Hyaluronic Acid Gel with Bupivacaine and MAP

Formulations as outlined in Table 6 were prepared essentially according to the method described in Example 1, with the exceptions that lidocaine was replaced by bupivacaine (CAS-number 2180-92-9, Cambrex, Karlskoga, Sweden) and that a hyaluronic acid gel with a modification degree of <1%, with a hyaluronic acid content of 12 mg/ml was used.

TABLE 6

| Formulation # | HA Gel [mg/ml] | Bupivacaine [mg/ml] | MAP [mg/ml] | G' at 1.0 Hz [Pa] |
|---|---|---|---|---|
| 6a | 12 | 0 | 0 | 62 |
| 6b | 12 | 1 | 0 | 90 |
| 6c | 12 | 1 | 0.3 | 61 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 6:
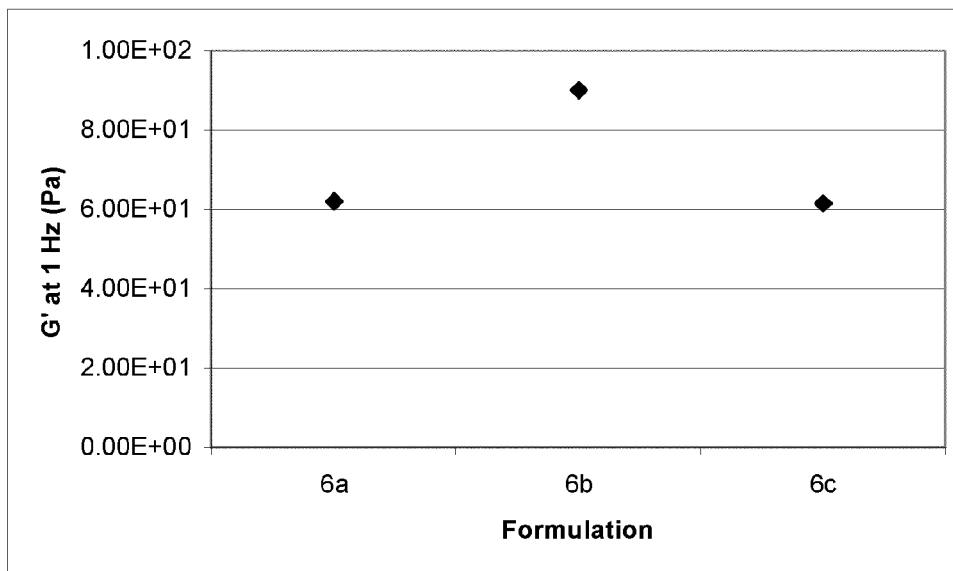
FIG. 6 is a graph showing the effect of MAP on a hyaluronic acid gel with bupivacaine.

The results are presented in FIG. 6. Bupivacaine has similar effect on the elastic modulus G' of the composition as lidocaine. MAP counteracts the effect on the elastic modulus G' of the composition caused by the local anesthetic upon sterilization by heat.

Example 7. Hyaluronic Acid Gel with Tetracaine and MAP

Formulations as outlined in Table 7 were prepared essentially according to the method described in Example 1 with the exception that lidocaine was replaced by tetracaine (CAS-number 136-47-0, Sigma Aldrich, St. Louis, USA) and the concentration of MAP was 0.3 mg/ml.

TABLE 7

| Formulation # | HA Gel [mg/ml] | Tetracaine [mg/ml] | MAP [mg/ml] | G' at 0.1 Hz [Pa] |
|---|---|---|---|---|
| 7a | 20 | 0 | 0 | 154 |
| 7b | 20 | 3 | 0 | 237 |
| 7c | 20 | 3 | 0.3 | 196 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 7:
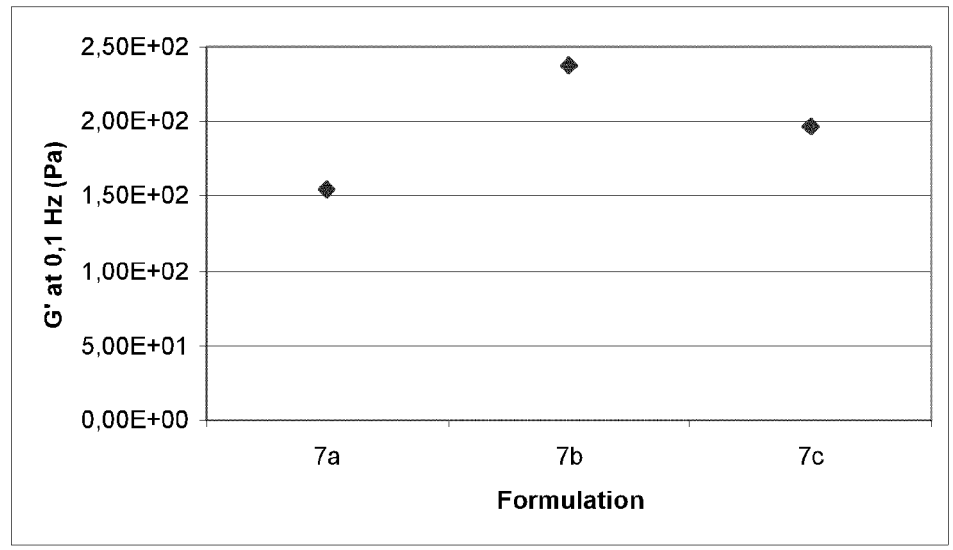
FIG. 7 is a graph showing the effect of MAP on a hyaluronic acid gel with tetracaine.

The results are presented in FIG. 7. Tetracaine has similar effect on the elastic modulus G' of the composition as lidocaine. MAP counteracts the effect on the elastic modulus G' of the composition caused by the local anesthetic upon sterilization by heat.

Example 8. Hyaluronic Acid Gel with Lidocaine and SAP

Formulations as outlined in Table 10 were prepared essentially according to the method described in Example 1, with the exception that Magnesium Ascorbyl Phosphate (MAP) was replaced by Sodium Ascorbyl Phosphate (SAP).

A stock-solution of SAP (CAS number 66170-10-3, Sigma Aldrich, St Louis, USA) was prepared by dissolving SAP in phosphate buffered saline (8 mM, 0.9% NaCl).

TABLE 8

| Formulation # | HA Gel [mg/ml] | Lidocaine [mg/ml] | SAP [mg/ml] | G' at 1.0 Hz [Pa] |
|---|---|---|---|---|
| 8a | 20 | 0 | 0 | 285 |
| 8b | 20 | 3 | 0 | 430 |
| 8c | 20 | 3 | 0.07 | 374 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~29).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 8:
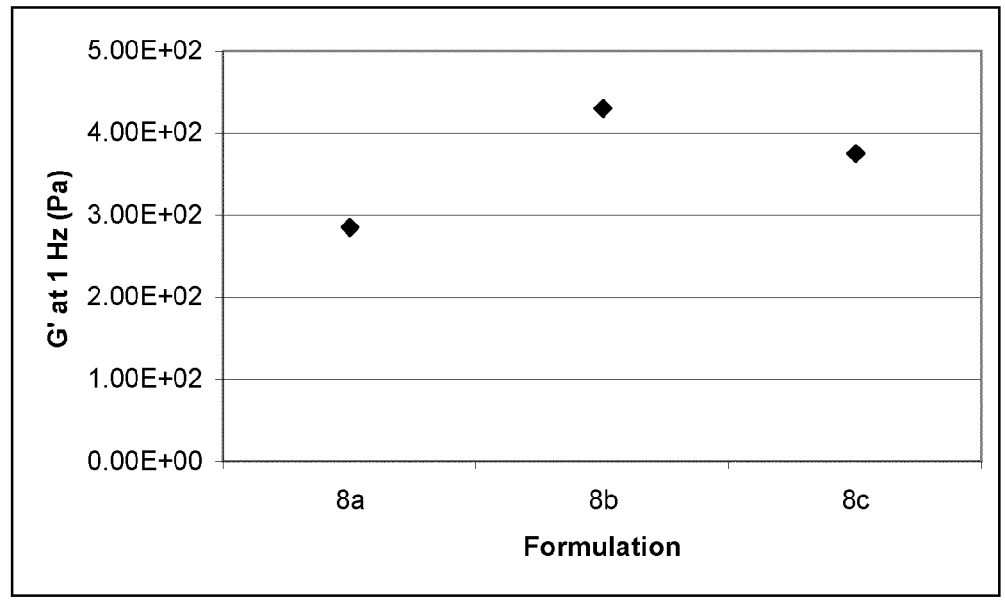
FIG. 8 is a graph showing the effect of SAP (Sodium Ascorbyl Phosphate) on a hyaluronic acid gel with lidocaine.

The results are presented in FIG. 8. SAP counteracts the effect on the elastic modulus G' of the composition caused by the local anesthetic upon sterilization by heat.

Example 9. Hyaluronic Acid Gel with Lidocaine and Methylsilanol Ascorbate

Formulations as outlined in Table 11 were prepared essentially according to the method described in Example 1, with the exceptions that Magnesium Ascorbyl Phosphate (MAP) was replaced by Ascorbosilane C (product number 078, Exsymol, Monaco) that contains methylsilanol ascorbate (CAS number 187991-39-5).

TABLE 9

| Formulation # | HA Gel [mg/ml] | Lidocaine [mg/ml] | Methylsilanol ascorbate [mg/ml] | G' at 1.0 Hz [Pa] |
|---|---|---|---|---|
| 9a | 20 | 0 | 0 | 194 |
| 9b | 20 | 3 | 0 | 269 |
| 9c | 20 | 3 | 0.3 | 134 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 9:
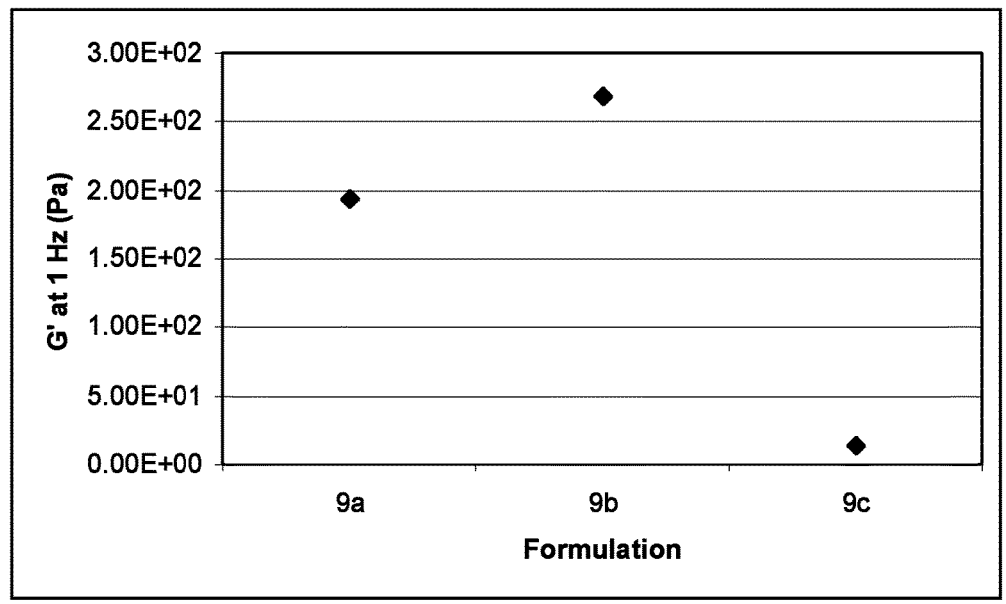
FIG. 9 is a graph showing the effect of Methylsilanol ascorbate on a hyaluronic acid gel with lidocaine.

The results are presented in FIG. 9. Methylsilanol ascorbate effectively counteracts the effect on the elastic modulus G' of the composition caused by the local anesthetic upon sterilization by heat.

Example 10. Non-Crosslinked Hyaluronic Acid with Bupivacaine and Ascorbyl Glucoside Formulations as outlined in Table 10 were prepared essentially according to the method described in Example 3, with the exception that lidocaine was replaced by bupivacaine and MAP was replaced by ascorbyl glucoside (CAS number 129499-78-1, CarboMer, Inc, San Diego, USA).

TABLE 10

| Formulation # | HA [mg/ml] | Bupivacaine [mg/ml] | Ascorbyl glucoside [mg/ml] | Zero shear viscosity $\eta_0$ [Pas] |
|---|---|---|---|---|
| 10a | 20 | 0 | 0 | 1.79 |
| 10b | 20 | 1 | 0 | 2.34 |
| 10c | 20 | 1 | 5 | 2.11 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22).

The viscosity of the formulations was studied using rotational viscometry using a Bohling VOR rheometer (Measure system C14).

Figure 10:
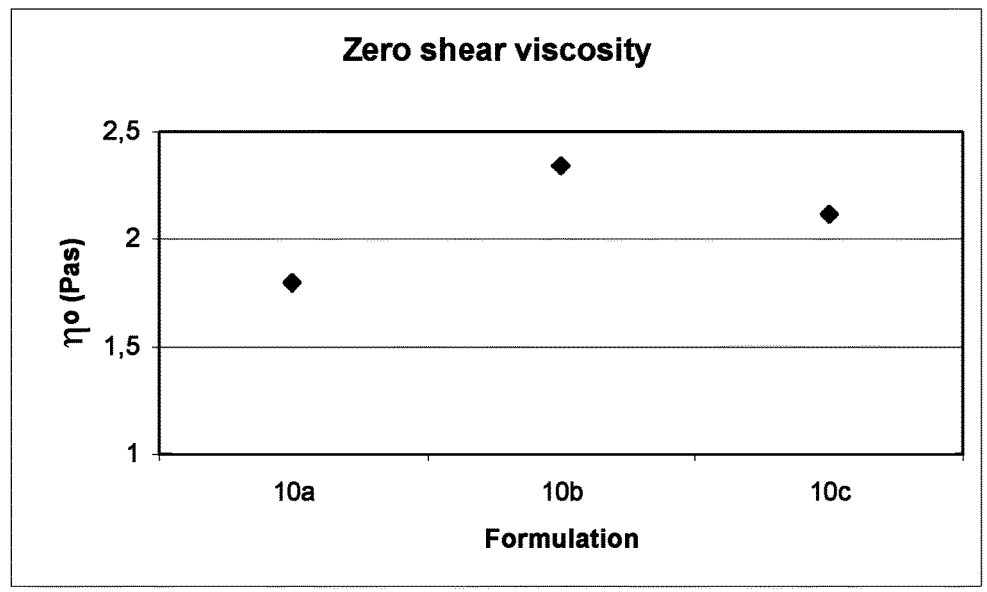
FIG. 10 is a graph showing the effect of Ascorbyl glucoside on a non-crosslinked hyaluronic acid with bupivacaine.

The results are presented in FIG. 10. Ascorbyl glucoside counteracts the effect on the viscosity of the composition caused by the local anesthetic upon sterilization by heat.

Example 11. Hyaluronic Acid Gel with Lidocaine and Different Concentrations of SAP Formulations as outlined in Table 11 were prepared essentially according to the method described in Example 8, with the exception that different concentrations of Sodium Ascorbyl Phosphate, SAP were used.

TABLE 11

| Formulation # | HA [mg/ml] | Lidocaine [mg/ml] | SAP [mg/ml] | G' at 1.0 Hz [Pa] |
|---|---|---|---|---|
| 11a | 20 | 0 | 0 | 159 |
| 11b | 20 | 3 | 0 | 290 |
| 11c | 20 | 3 | 0.005 | 287 |
| 11d | 20 | 3 | 0.1 | 256 |
| 11e | 20 | 3 | 0.5 | 175 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22).

Figure 11:
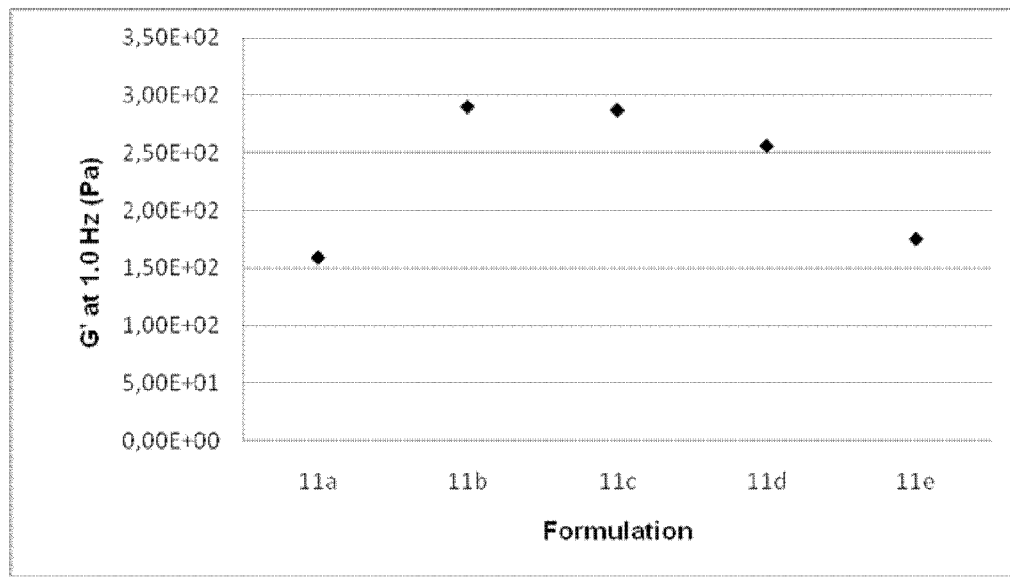
FIG. 11 is a graph showing the effect of different concentrations of SAP on a hyaluronic acid gel with lidocaine.

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR. The results are presented in FIG. 11. SAP counteracts the effect on the elastic modulus G' of the composition caused by the local anesthetic upon sterilization by heat. The higher the concentration of SAP the greater is the effect.

Example 12. Hyaluronic Acid Gel with Tetracaine and L-Ascorbic Acid Acetonide

Formulations as outlined in Table 12 were prepared essentially according to the method described in Example 7 with the exceptions that MAP was replaced by L-ascorbic acetonide (CAS-number 15042-01-0, Carbosynth, Berkshire, UK) and a higher concentration of the derivative was used.

TABLE 12

| Formulation # | HA Gel [mg/ml] | Tetracaine [mg/ml] | L-Ascorbic acid acetonide [mg/ml] | G' at 1.0 Hz [Pa] |
|---|---|---|---|---|
| 12a | 20 | 0 | 0 | 266 |
| 12b | 20 | 3 | 0 | 345 |
| 12c | 20 | 3 | 1.0 | 25 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~5).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 12:
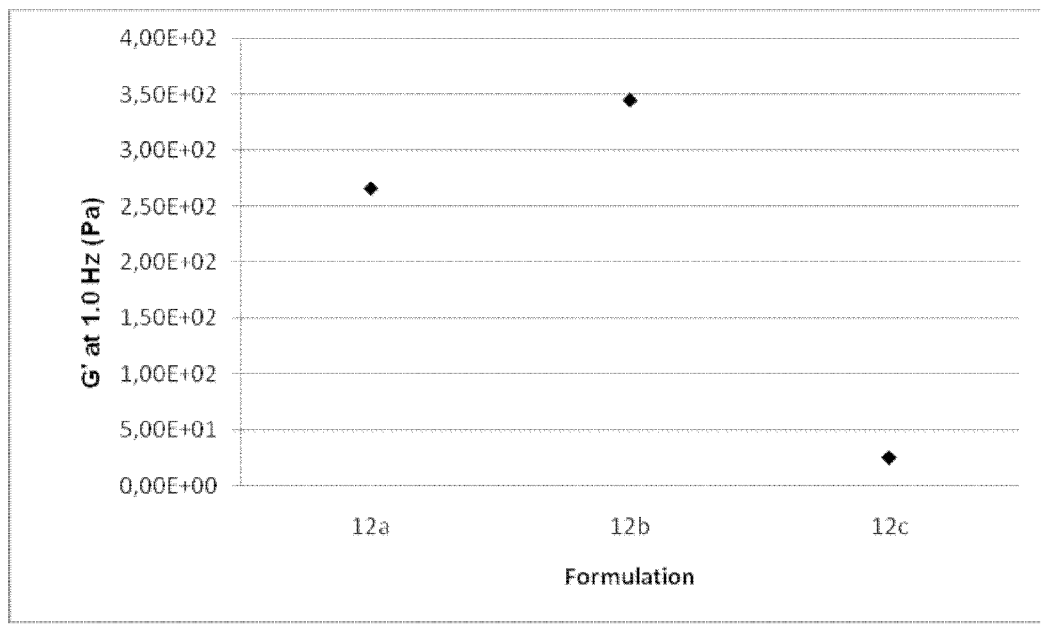
FIG. 12 is a graph showing the effect of L-Ascorbic acid acetonide on a hyaluronic acid gel with tetracaine.

The results are presented in FIG. 12. L-Ascorbic acetonide effectively counteracts the effect on the elastic modulus G' of the composition caused by the local anesthetic upon sterilization by heat.

Example 13. Hyaluronic Acid Gel with a Higher Degree of Modification with Lidocaine and SAP Formulations as outlined in Table 13 were prepared essentially according to the method described in Example 1, with the exceptions that a hyaluronic acid gel with a higher degree of modification (approximately 7%) was used, that Magnesium Ascorbyl Phosphate (MAP) was replaced by Sodium Ascorbyl Phosphate, SAP (CAS number 66170-10-3, Sigma Aldrich, St. Louis, USA), and that another concentration of the derivative was used.

TABLE 13

| Formulation # | HA Gel [mg/ml] | Lidocaine [mg/ml] | SAP [mg/ml] | G' at 1.0 Hz [Pa] |
|---|---|---|---|---|
| 13a | 20 | 0 | 0 | 1110 |
| 13b | 20 | 3 | 0 | 1260 |
| 13c | 20 | 3 | 0.1 | 1150 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~32).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 13:
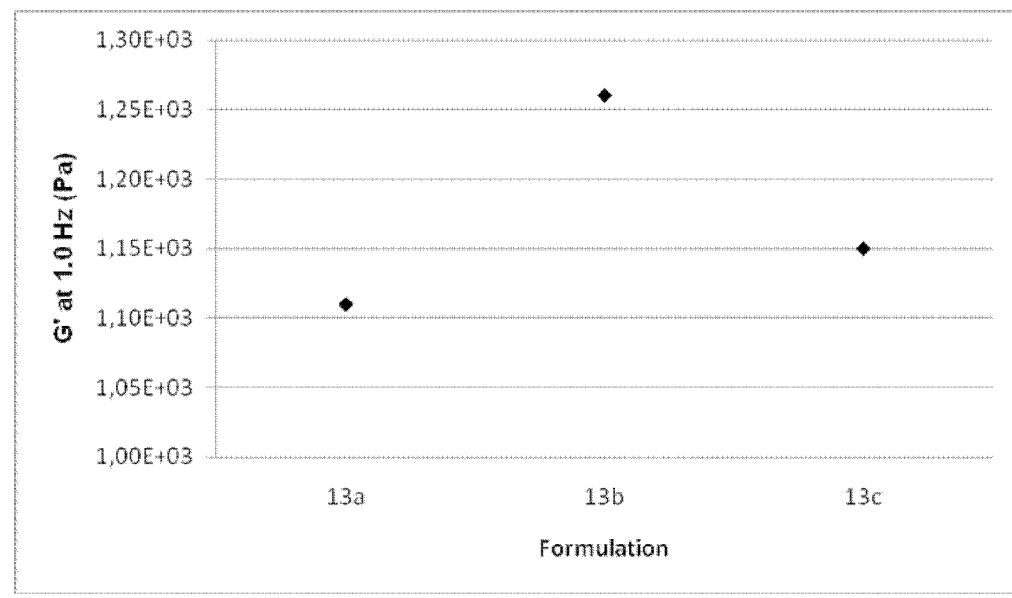
FIG. 13 is a graph showing the effect of SAP on a hyaluronic acid gel with lidocaine.

The results are presented in FIG. 13. SAP counteracts the effect on the elastic modulus G' of the composition caused by the local anesthetic upon sterilization by heat.

Example 14. Non-Crosslinked Hyaluronic Acid with Lidocaine and Aminopropyl Ascorbyl Phosphate Formulations as outlined in Table 14 were prepared essentially according to the method described in Example 3, with the exceptions that Magnesium Ascorbyl Phosphate (MAP) was replaced by Aminopropyl Ascorbyl Phosphate (Macro Care, South Korea) and that a higher concentration of the derivative was used.

TABLE 14

| Formulation # | HA [mg/ml] | Lidocaine [mg/ml] | Aminopropyl Ascorbyl phosphate [mg/ml] | Zero shear viscosity $\eta_0$ [Pas] |
|---|---|---|---|---|
| 14a | 20 | 0 | 0 | 2.29 |
| 14b | 20 | 3 | 0 | 3.45 |
| 14c | 20 | 3 | 1.5 | 1.76 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22).

The viscosity of the formulations was studied using rotational viscometry using a Bohling VOR rheometer (Measure system PP 30, Gap 1.00 mm).

Figure 14:
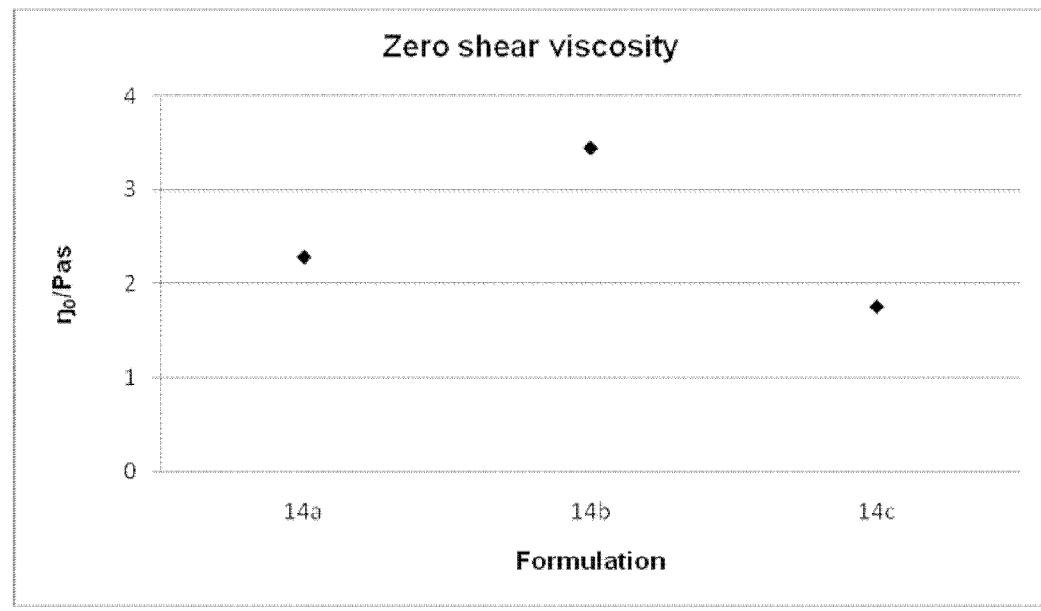
FIG. 14 is a graph showing the effect of Aminopropyl Ascorbyl Phosphate on a non-crosslinked hyaluronic acid with lidocaine.

The results are presented in FIG. 14. Aminopropyl Ascorbyl phosphate effectively counteracts the effect on the viscosity of the composition caused by the local anesthetic upon sterilization by heat.

Example 15. Hyaluronic Acid Gel with Lidocaine and Ascorbyl Glucoside

Formulations as outlined in Table 15 were prepared essentially according to the method described in Example 1 with the exceptions that Magnesium Ascorbyl Phosphate (MAP) was replaced by Ascorbyl glucoside (CarboMer, Inc, San Diego, USA) and another concentration of the derivative was used.

TABLE 15

| Formulation # | HA Gel [mg/ml] | Lidocaine [mg/ml] | Ascorbyl glucoside [mg/ml] | G' at 1.0 Hz [Pa] |
|---|---|---|---|---|
| 15a | 20 | 3 | 0 | 833 |
| 15b | 20 | 3 | 0.08 | 777 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~23).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 15:
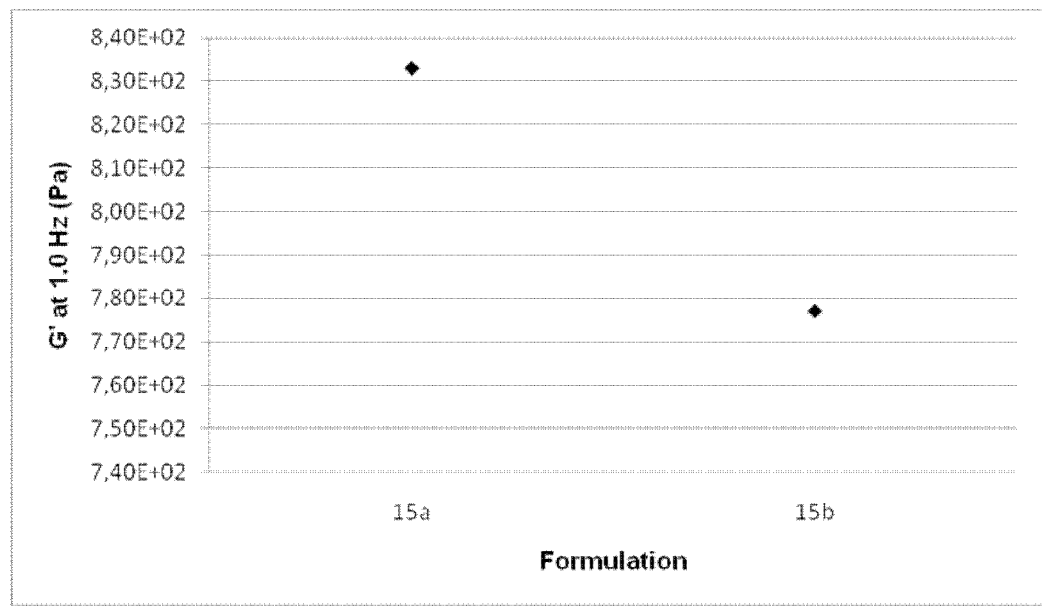
FIG. 15 is a graph showing the effect of Ascorbyl glucoside on a hyaluronic acid gel with lidocaine.

The results are presented in FIG. 15. Ascorbyl glucoside counteracts the effect on the elastic modulus G' of the composition caused by the local anesthetic upon sterilization by heat.

Example 16. Hyaluronic Acid Gel with Lidocaine and Ascorbyl Glucoside

Formulations as outlined in Table 16 were prepared essentially according to the method described in Example 15 with the exceptions that a hyaluronic acid gel with a modification degree of <1%, with a hyaluronic acid content of 12 mg/ml was used and that a higher concentration of the derivative was used.

TABLE 16

| Formulation # | HA Gel [mg/ml] | Lidocaine [mg/ml] | Ascorbyl glucoside [mg/ml] | G' at 1.0 Hz [Pa] |
|---|---|---|---|---|
| 16a | 12 | 3 | 0 | 84 |
| 16b | 12 | 3 | 0.17 | 80 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~23).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 16:
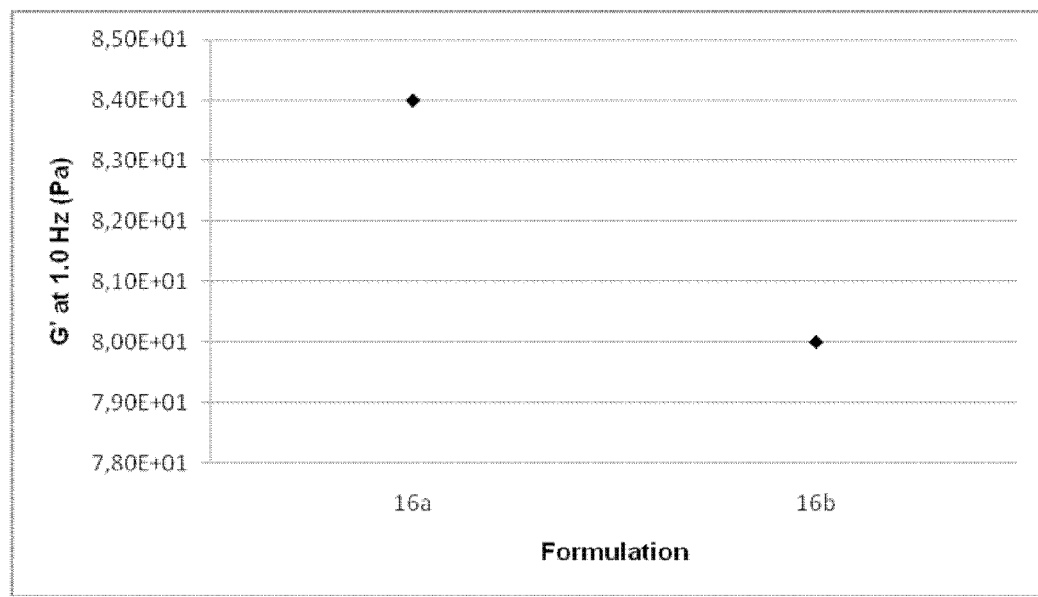
FIG. 16 is a graph showing the effect of Ascorbyl glucoside on a hyaluronic acid gel with lidocaine.

The results are presented in FIG. 16. Ascorbyl glucoside counteracts the effect on the elastic modulus G' of the composition caused by the local anesthetic upon sterilization by heat.

Example 17. Hyaluronic Acid Gel with Lidocaine and Ascorbyl Glucoside

Formulations as outlined in Table 17 were prepared essentially according to the method described in Example 15 with the exceptions that Ascorbyl glucoside from another manufacturer (Hayashibara Biochemical Laboratories, Inc, Okayama, Japan) was used and that higher concentrations of the derivative were used. In this example a hyaluronic acid gel with a hyaluronic acid content of 16 mg/ml was used.

TABLE 17

| Formulation # | HA Gel [mg/ml] | Lidocaine [mg/ml] | Ascorbyl glucoside [mg/ml] | G' at 1.0 Hz [Pa] |
|---|---|---|---|---|
| 17a | 16 | 3 | 0 | 330 |
| 17b | 16 | 3 | 0.8 | 314 |
| 17c | 16 | 3 | 8.0 | 301 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~23).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 17:
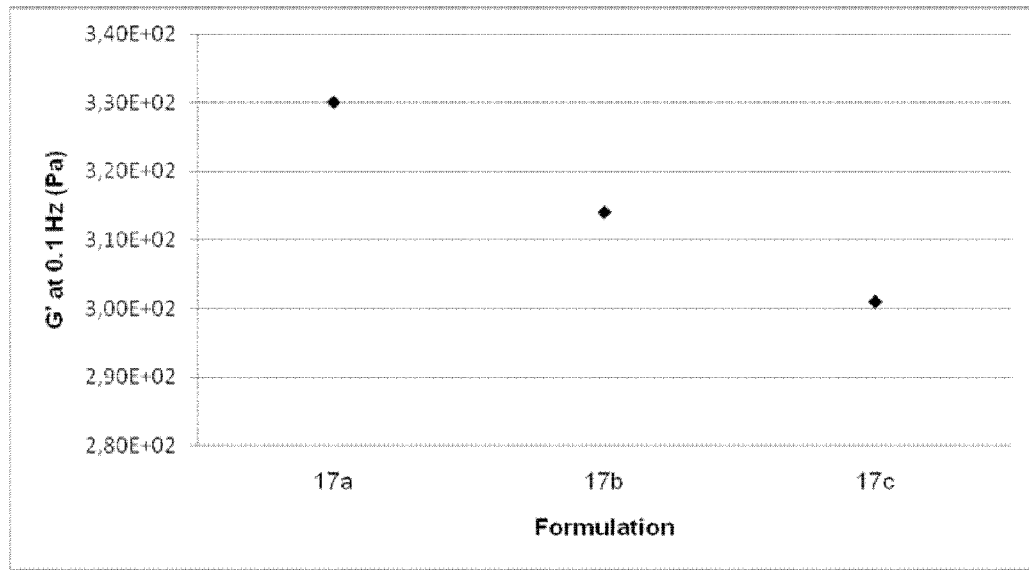
FIG. 17 is a graph showing the effect of Ascorbyl glucoside on a hyaluronic acid gel with lidocaine.

The results are presented in FIG. 17. Ascorbyl glucoside counteracts the effect on the elastic modulus G' of the composition caused by the local anesthetic upon sterilization by heat.

Example 18. Hyaluronic Acid Gels with Different Degrees of Modification with Lidocaine and MAP Formulations as outlined in Table 18 were prepared essentially according to the method described in Example 1 with the exception that another concentration of MAP was used. In this example hyaluronic acid gels with different degrees of modification were used.

TABLE 18

| Formulation # | HA Gel/Solution [mg/ml] | Degree of modification [mole %] | Lidocaine [mg/ml] | MAP [mg/ml] | G' at 1.0 Hz [Pa] | Reduction in G' [%] |
|---|---|---|---|---|---|---|
| 18a | 20 | <1 | 3 | 0 | 66 | — |
| 18b | 20 | <1 | 3 | 0.3 | 38 | 43 |
| 18c | 20 | 1 | 3 | 0 | 269 | — |
| 18d | 20 | 1 | 3 | 0.3 | 220 | 18 |
| 18e | 20 | 7 | 3 | 0 | 417 | — |
| 18f | 20 | 7 | 3 | 0.3 | 388 | 7 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~22).

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 18:
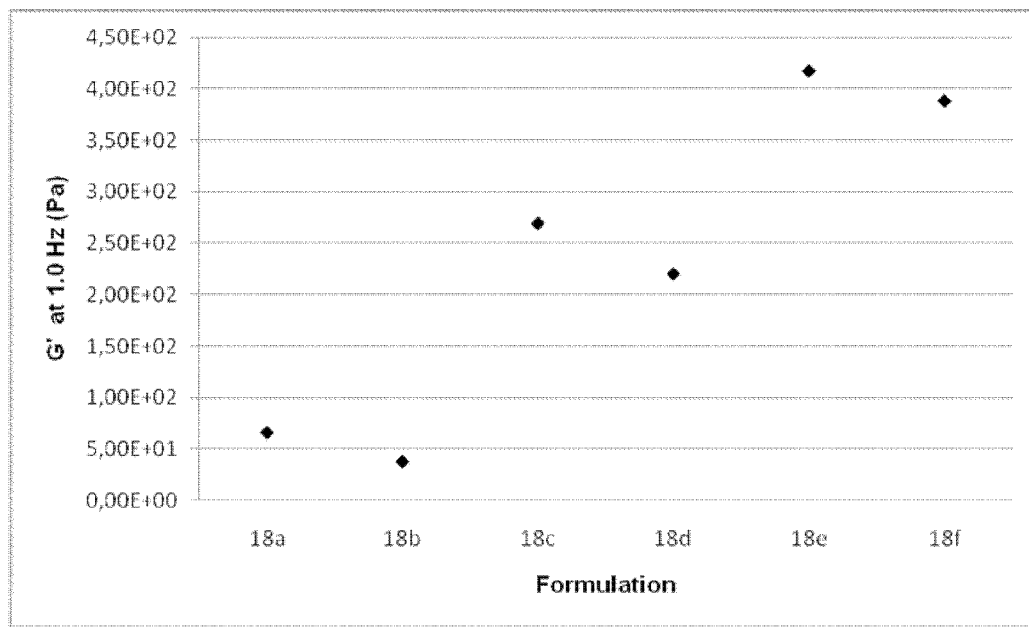
FIG. 18 is a graph showing the effect of MAP on a hyaluronic acid gels with lidocaine.

The results are presented in FIG. 18. MAP counteracts the effect on the elastic modulus G' of the composition caused by the local anesthetic upon sterilization by heat. The effect is more pronounced in the formulations with a lower degree of modification.

Example 19. Stability Study for 14 Days in 60° C.

Hyaluronic Acid Gel with a Higher Degree of Modification with Lidocaine and SAP

Formulations as outlined in Table 19 were prepared essentially according to the method described in Example 2, with the exceptions that Magnesium Ascorbyl Phosphate (MAP) was replaced by Sodium Ascorbyl Phosphate, SAP and that a lower concentration of the derivative was used.

TABLE 19

| Formulation # | HA Gel [mg/ml] | Lidocaine [mg/ml] | SAP [mg/ml] |
|---|---|---|---|
| 19a | 20 | 0 | 0 |
| 19b | 20 | 3 | 0 |
| 19c | 20 | 3 | 0.1 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0$~32).

A stability study in 60° C. for 14 days was performed with sampling at 0, 3, 7, 11 and 14 days.

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 19:
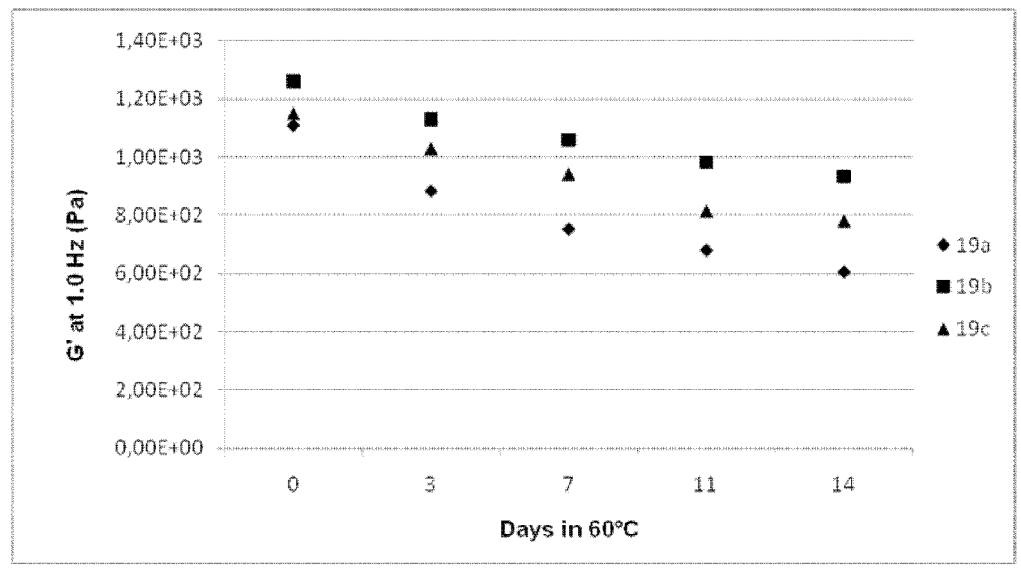
FIG. 19 is a graph showing the effect of SAP on a hyaluronic acid gel with lidocaine in a stability study.

The results are presented in FIG. 19. The stability of the composition is not increased by SAP. The degradation rate of the composition with SAP corresponds to the composition without SAP.

Example 20. Stability Study for 14 Days in 60° C.

Hyaluronic Acid Gel with Lidocaine and Ascorbyl Glucoside

Formulations as outlined in Table 20 were prepared essentially according to the method described in Example 1, with the exceptions that Magnesium Ascorbyl Phosphate (MAP) was replaced by Ascorbyl glucoside (CarboMer, Inc, San Diego, USA) and that another concentration of the derivative was used.

TABLE 20

| Formulation # | HA Gel [mg/ml] | Lidocaine [mg/ml] | Ascorbyl glucoside [mg/ml] |
| --- | --- | --- | --- |
| 20a | 20 | 3 | 0 |
| 20b | 20 | 3 | 0.17 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0\sim22$).

A stability study in 60° C. for 14 days was performed with sampling at 0, 7 and 14 days.

The gel content was determined by adding an excess of saline to a known amount of the preparation and dispersing the gel thoroughly to form a dilute suspension. The diluted suspension of the gel was filtered through a 0.22 mm filter and the concentration of HA in the filtrate, "the extractable part", was determined using the carbazol method. The gel content was calculated as the fraction of HA in the filler that cannot pass through the 0.22 mm filter when filtering the diluted suspension of the product.

Figure 20:
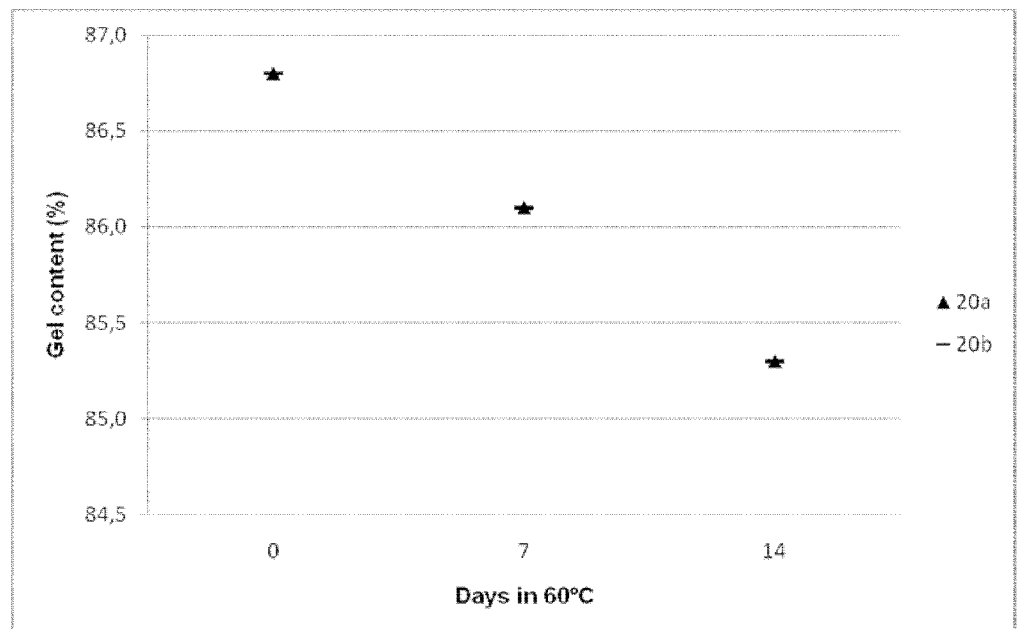
FIG. 20 is a graph showing the effect of Ascorbyl glucoside on a hyaluronic acid gel with lidocaine in a stability study.

The results are presented in FIG. 20. There is no change in stability for the composition with Ascorbyl glucoside compared to the formulation without Ascorbyl glucoside.

Example 21. Stability Study for 14 Days in 60° C.

Hyaluronic Acid Gel with Lidocaine, MAP or Ascorbyl Glucoside

Formulations as outlined in Table 21 were prepared essentially according to the method described in Example 1, with the exceptions that MAP or Ascorbyl glucoside (CarboMer, Inc, San Diego, USA) were used and that a hyaluronic acid gel with a modification degree of <1%, with a hyaluronic acid content of 12 mg/ml was used.

TABLE 21

| Formulation # | HA Gel [mg/ml] | Lidocaine [mg/ml] | MAP [mg/ml] | Ascorbyl glucoside [mg/ml] |
| --- | --- | --- | --- | --- |
| 21a | 12 | 3 | 0 | 0 |
| 21b | 12 | 3 | 0.07 | 0 |
| 21c | 12 | 3 | 0 | 0.07 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0\sim26$).

A stability study in 60° C. for 14 days was performed with sampling at 0, 3, 7, 11 and 14 days.

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 21:
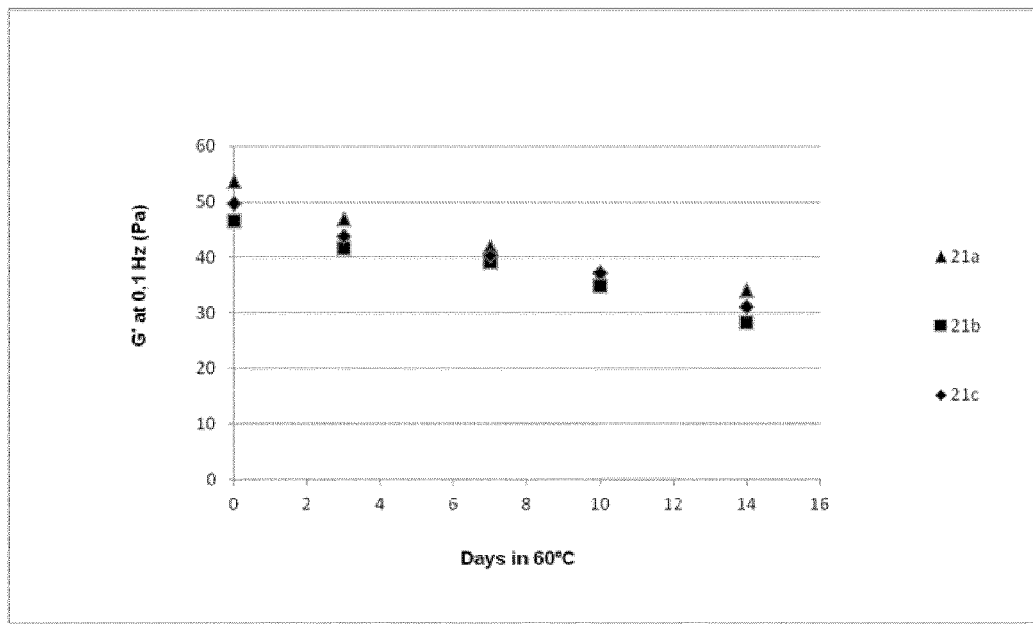
FIG. 21 is a graph showing the effect of MAP or Ascorbyl glucoside on a hyaluronic acid gel with lidocaine in a stability study.

The results are presented in FIG. 21. The stability of the composition is unaffected by Ascorbyl glucoside. In the composition with MAP a slight decrease in the stability is seen. However, the inventors have found that the stability of the compositions is still acceptable and that advantages associated with adding the ascorbic acid derivative outweigh the slight decrease in stability caused by the addition.

Example 22. Stability Study for 16 Hours in 90° C.

Hyaluronic Acid Gel with Lidocaine and Ascorbyl Glucoside

Formulations as outlined in Table 22 were prepared essentially according to the method described in Example 1, with the exceptions that Magnesium Ascorbyl Phosphate (MAP) was replaced by Ascorbyl glucoside (Hayashibara Biochemical Laboratories, Inc, Okayama, Japan) and that other concentrations of the derivative were used. In this example a hyaluronic acid gel with a hyaluronic acid content of 16 mg/ml was used.

TABLE 22

| Formulation # | HA Gel [mg/ml] | Lidocaine [mg/ml] | Ascorbyl glucoside [mg/ml] |
| --- | --- | --- | --- |
| 22a | 16 | 3 | 0 |
| 22b | 16 | 3 | 0.17 |
| 22c | 16 | 3 | 8.0 |

The pH values of the formulations were adjusted to 7.5±0.2 and the formulations were filled in 1 ml glass syringes (BD Hypak SCF) and autoclaved in a Getinge GEV 6610 ERC-1 autoclave ($F_0\sim26$).

A stability study in 90° C. for 16 hours was performed with sampling at 0, 8 and 16 hours.

The rheological properties of the formulations were analysed using a Bohlin VOR Reometer (Measure system PP 30, Gap 1.00 mm). Initially a strain sweep was made to find the linear viscoelastic region (LVR) and then the viscoelastic properties were measured within the LVR.

Figure 22:
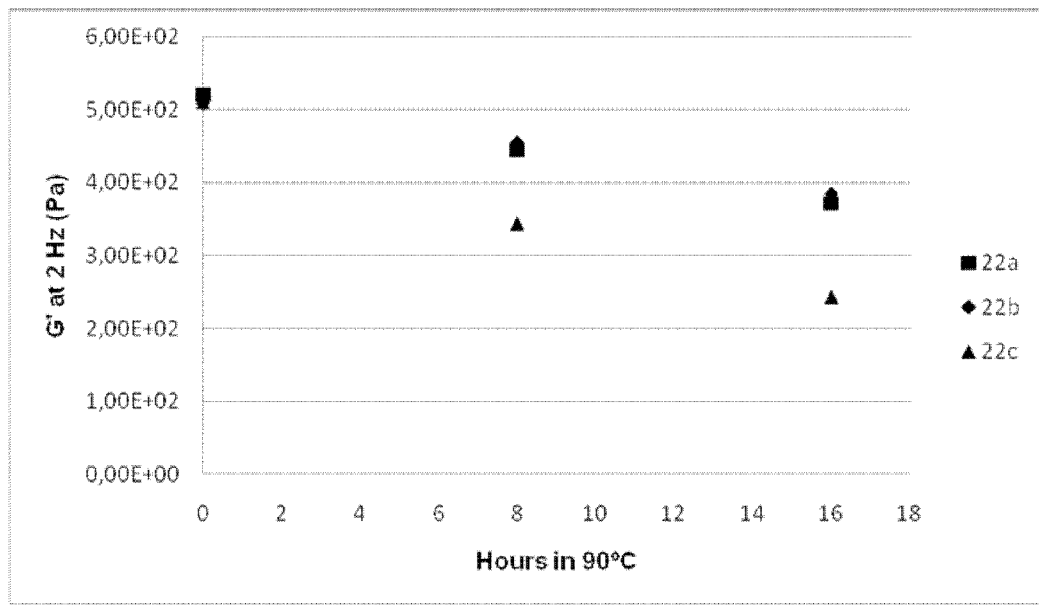
FIG. 22 is a graph showing the effect of Ascorbyl glucoside on a hyaluronic acid gel with lidocaine in a stability study.

The results are presented in FIG. 22. Ascorbyl glucoside in the lower concentration does not affect the stability of the composition. The higher concentration of Ascorbyl glucoside decreases the stability of the composition. From these results it was concluded a concentration of Ascorbyl glucoside of below 5 mg/ml is preferred, since higher concentrations may result in unnecessary decrease of stability of the hyaluronic acid composition.

The invention claimed is:

1. A method for preventing or reducing the effect of a local anesthetic on the viscosity and/or elastic modulus G' of an injectable hyaluronic acid composition due to sterilization by heat, said method comprising adding to the composition an ascorbic acid derivative selected from the group consisting of ascorbyl phosphates, ascorbyl sulfates and ascorbyl glycosides, wherein said injectable hyaluronic acid composition further comprises
a hyaluronic acid gel and
a therapeutically relevant concentration of a local anesthetic selected from the group consisting of amide and ester type local anesthetics or a combination thereof, and
wherein the ascorbic acid derivative is added to the composition to a concentration in the range of 0.01 to 5 mg/ml,
wherein the hyaluronic acid gel is crosslinked by modification with a chemical crosslinking agent and wherein a degree of modification of the hyaluronic acid gel is less than 2 mol %,
wherein the hyaluronic acid composition does not exhibit increased stability compared to the same composition without an ascorbic acid derivative,
wherein said local anesthetic is lidocaine.

2. The method according to claim 1, wherein said ascorbic acid derivative is selected from the group consisting of ascorbyl phosphates and ascorbyl glycosides, or a combination thereof.

3. The method according to claim 1, wherein the concentration of said ascorbic acid derivative is in the range of 0.01 to 0.5 mg/ml.

4. The method according to claim 2, wherein said ascorbic acid derivative is selected from the group consisting of sodium ascorbyl phosphate (SAP) and magnesium ascorbyl phosphate (MAP) and the concentration of said sodium ascorbyl phosphate (SAP) or magnesium ascorbyl phosphate (MAP) is in the range of 0.01 to 1 mg/ml.

5. The method according to claim 2, wherein said ascorbic acid derivative is ascorbyl glucoside and the concentration of said ascorbyl glucoside is in the range of 0.01 to 1 mg/ml.

6. A method of manufacturing a sterilized hyaluronic acid composition comprising:
a) mixing a hyaluronic acid gel, a therapeutically relevant concentration of a local anesthetic selected from the group consisting of amide and ester type local anesthetics or a combination thereof, and an ascorbic acid derivative selected from the group consisting of ascorbyl phosphates, ascorbyl sulfates and ascorbyl glycosides, in an amount which prevents or reduces the effect on the viscosity and/or elastic modulus G' of the composition caused by the local anesthetic upon sterilization by heat, wherein the concentration of said ascorbic acid derivative in the composition is in the range of 0.01 to 5 mg/ml, and
b) subjecting the mixture to sterilization by autoclaving at a $F_0$-value $\geq 4$,
wherein the hyaluronic acid gel is crosslinked by modification with a chemical crosslinking agent and wherein a degree of modification of the hyaluronic acid gel is less than 2 mol %,
wherein the hyaluronic acid composition does not exhibit increased stability compared to the same composition without an ascorbic acid derivative, and
wherein said local anesthetic is lidocaine.

* * * * *